United States Patent
Irie et al.

(10) Patent No.: US 12,186,320 B2
(45) Date of Patent: Jan. 7, 2025

(54) THERAPEUTIC AGENT CONTAINING PYRAZOLO[3,4-D]PYRIMIDINE COMPOUND AS ACTIVE INGREDIENT

(71) Applicant: TAIHO PHARMACEUTICAL CO., LTD., Chiyoda-ku (JP)

(72) Inventors: Hiroki Irie, Ibaraki (JP); Yayoi Fujioka, Ibaraki (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 912 days.

(21) Appl. No.: 17/271,125

(22) PCT Filed: Aug. 28, 2019

(86) PCT No.: PCT/JP2019/033595
§ 371 (c)(1),
(2) Date: Feb. 24, 2021

(87) PCT Pub. No.: WO2020/045461
PCT Pub. Date: Mar. 5, 2020

(65) Prior Publication Data
US 2021/0252000 A1  Aug. 19, 2021

(30) Foreign Application Priority Data

Aug. 29, 2018  (JP) ................................ 2018-160014

(51) Int. Cl.
| | |
|---|---|
| *A61K 31/519* | (2006.01) |
| *A61K 9/00* | (2006.01) |
| *A61P 35/00* | (2006.01) |
| *C07K 16/32* | (2006.01) |

(52) U.S. Cl.
CPC .......... *A61K 31/519* (2013.01); *A61K 9/0053* (2013.01); *A61P 35/00* (2018.01); *C07K 16/32* (2013.01)

(58) Field of Classification Search
CPC .............................. C07K 16/32; A61K 31/519
See application file for complete search history.

(56) References Cited

U.S. PATENT DOCUMENTS

| 9,920,060 B2* | 3/2018 | Kawai et al. ........ A61K 31/519 |
| 2016/0045596 A1 | 2/2016 | Geretti et al. |
| 2017/0080087 A1 | 3/2017 | Espelin et al. |
| 2017/0217970 A1* | 8/2017 | Kawai et al. ........ C07D 487/04 |
| 2018/0201615 A1 | 7/2018 | Kawai et al. |

FOREIGN PATENT DOCUMENTS

| WO | WO2016022723 A1 * | 2/2016 | ............ C07K 16/32 |
| WO | WO 2017/038838 A1 | 3/2017 | |
| WO | WO 2018/159613 A1 | 9/2018 | |

OTHER PUBLICATIONS

Brent N. Rexer et al., (Intrinsic and Acquired Resistance to HER2-Targeted Therapies in HER2 Gene-Amplified Breast Cancer: Mechanisms and Clinical Implications, CritRevOncog., vol. 17, Issue 1, 2012, pp. 1-16., (DOI: 10.1615/CritRevOncog.v17.i1.2012) (Year: 2012).*
International Search Report issued on Nov. 12, 2019 in PCT/JP2019/033595 filed on Aug. 28, 2019, 1 page.
Yan et al., "HER2 aberrations in cancer: Implications for therapy", Cancer Treatment Reviews, 2014, vol. 40, pp. 770-780.
Fink et al., "Survival of HER2-Positive Breast Cancer Cells: Receptor Signaling to Apoptotic Control Centers", Genes & Cancer, 2013, vol. 4, No. 5-6, pp. 187-195.
Neve et al., "Effects of oncogenic ErbB2 on G1 cell cycle regulators in breast tumour cells", Oncogene, 2000, vol. 19, pp. 1647-1656.
Moasser "The oncogene HER2: its signaling and transforming functions and its role in human cancer pathogenesis", Oncogene, 2007, vol. 26, pp. 6469-6487.
De Melo Gagliato et al., "Mechanisms of resistance and sensitivity to anti-HER2 therapies in HER2+ breast cancer", Oncotarget, 2016, vol. 7, No. 39, pp. 64431-64446.
Hubalek et al., "Resistance to HER2-targeted therapy: mechanisms of trastuzumab resistance and possible strategies to overcome unresponsiveness to treatment", Wien Med Wochenschr, 2010, vol. 160, No. 19-20, pp. 506-512.
Extended European Search report issued on May 18, 2022, in European Patent Application No. 19856279.5, 7 pages.

* cited by examiner

*Primary Examiner* — Paul V Ward
(74) *Attorney, Agent, or Firm* — Oblon, McClelland, Maier & Neustadt, L.L.P.

(57) ABSTRACT

Provided is an anti-tumor agent for the treatment of a HER2-positive tumor that is tolerant to other anti-tumor agents or an intractable HER2-positive tumor. More specifically provided is a therapeutic agent for a HER2-positive tumor that is tolerant to other anti-tumor agents or an intractable HER2-positive tumor, which contains a pyrazolo [3,4-d]pyrimidine compound or a salt thereof as an active ingredient.

7 Claims, 1 Drawing Sheet

THERAPEUTIC AGENT CONTAINING PYRAZOLO[3,4-D]PYRIMIDINE COMPOUND AS ACTIVE INGREDIENT

This application claims benefit of the filing date of PCT/JP2019/033595 filed Aug. 28, 2019 and claims priority to Japanese application 2018-160014, filed Aug. 29, 2018, the contents of both applications are incorporated herein in their entirety.

TECHNICAL FIELD

The present invention relates to a therapeutic agent for a HER2-positive tumor that is resistant or intractable to other antitumor agents, which contains a pyrazolo[3,4-d]pyrimidine compound or a salt thereof as an active ingredient.

BACKGROUND ART

HER2 (also called ErbB2) is a receptor tyrosine kinase that belongs to the ErbB family.

HER2 is considered as a cancer-causing gene (Non-patent document 1), and amplification, mutation, overexpression and the like of HER2 gene have been reported in various cancers (Non-patent document 2). In cancer cells associated with such abnormal expression/overexpression of HER2 gene, activation of HER2 signaling and signaling in the downstream pathways are reported to increase survival/growth signaling and the like in the cancer cells (Non-patent documents 3 and 4).

An inhibitor that can suppress the kinase activity of HER2 would therefore presumably exert an anti-tumor effect by inhibiting signal transduction by HER2 and inhibiting signal transduction in the downstream pathways in the cancer cells, and thus considered to be effective as a cancer-treating drug.

As drugs that target HER2, anti-HER2 antibodies (trastuzumab, pertuzumab) and anti-HER2 antibody-drug conjugates (trastuzumab emtansine, etc.) have already been approved as therapeutic drugs for HER2-positive breast cancer. However, emergence of patients resistant to these drugs has also been reported (Non-patent documents 5 and 6), and thus a drug that exerts an anti-tumor effect in patients showing resistant to these drugs seems to be beneficial as a cancer-treating drug.

While pyrazolo[3,4-d]pyrimidine represented by General formula (I) or a salt thereof is known as a HER2 inhibitor (Patent document 1), its anti-tumor effect on a HER2-positive tumor that is resistant or intractable to the existing drugs is yet unknown.

PRIOR ART DOCUMENTS

Patent Document

Patent document 1: International Patent Application Publication WO2017/038838

Non-Patent Documents

Non-patent document 1: Oncogene, 26 (45), pp. 6469-6487 (2007)
Non-patent document 2: Cancer Treat. Rev., 40, pp. 770-780 (2014)
Non-patent document 3: Genes Cancer, 4, pp. 187-195 (2013)
Non-patent document 4: Oncogene, 19, pp. 1647-1656 (2000)
Non-patent document 5: Wien Med Wochenschr, 160 (19-20), pp. 506-512 (2010)
Non-patent document 6: Oncotarget, 7 (39), pp. 64431-64446 (2016)

SUMMARY OF INVENTION

Problem to be Solved by the Invention

In consideration of the above-described situation, an antitumor agent for treating a HER2-positive tumor that is resistant or intractable to other antitumor agents is strongly desired.

Means for Solving the Problem

Embodiments of the present invention comprise [1]-[9] below.

[1] A therapeutic agent for a HER2-positive tumor that is resistant or intractable to other antitumor agents, the therapeutic agent comprising a pyrazolo[3,4-d]pyrimidine compound represented by General formula (I) below or a salt thereof as an active ingredient:

[Chemical formula 1]

(wherein, X represents a saturated, optionally substituted nitrogen-containing 4-10-membered heterocyclic group;
Y represents $-C(R_4)=C(R_5)(R_6)$;
$Z_1$, $Z_2$, $Z_3$ and $Z_4$ identically or differently represent a hydrogen atom, a halogen atom, a cyano group, a C2-C6 alkenyl group, an optionally substituted C1-C6 alkoxy group, an optionally substituted C1-C6 alkyl group, an optionally substituted amino group, an optionally substituted C3-C7 cycloalkyl group, a C6-C14 aromatic hydrocarbon group or an unsaturated 4-14-membered heterocyclic group, or $Z_1$ and $Z_2$ or $Z_3$ and $Z_4$ may form, together with carbon atoms that bind thereto, a benzene ring or a saturated or unsaturated 5-7-membered heterocycle;
W represents $-CH_2-$, an oxygen atom or $-NH-$;
n represents an integer of 0 to 2;
$R_1$ represents an optionally substituted amino group;
$R_2$ and $R_3$ identically or differently represent a hydrogen atom, an optionally substituted C1-C6 alkoxy group, an optionally substituted C1-C6 alkyl group or an option- ally substituted C6-C14 aromatic hydrocarbon group, or $R_2$ and $R_3$ may form, together with a nitrogen atom that binds thereto, a saturated, optionally substituted nitrogen-containing 4-8-membered heterocyclic group; and $R_4$, $R_5$ and $R_6$ identically or differently represent a hydrogen atom or an optionally substituted C1-C6 alkyl group).

[2] The therapeutic agent according to [1], wherein the pyrazolo[3,4-d]pyrimidine compound is a compound represented by General formula (I), wherein:
X is a saturated nitrogen-containing 4-8-membered heterocyclic group which may have a halogen atom or a C1-C6 alkyl group as a substituent;
Y is —C($R_4$)=C($R_5$)($R_6$);
$Z_1$, $Z_2$, $Z_3$ and $Z_4$ are identically or differently a hydrogen atom, a halogen atom, a cyano group, a C2-C6 alkenyl group, a C1-C6 alkoxy group which may be substituted with a halogen atom, a C1-C6 alkyl group, an amino group which may be substituted with a C1-C6 alkyl group, a C3-C7 cycloalkyl group or an unsaturated 4-6-membered heteromonocyclic group having one oxygen atom, or $Z_1$ and $Z_2$ or $Z_3$ and $Z_4$ may form, together with carbon atoms that bind thereto, a benzene ring or a saturated or unsaturated 5-7-membered heterocycle;
W is —CH$_2$—, an oxygen atom or —NH—;
n is 0;
$R_1$ is an amino group;
$R_2$ and $R_3$ are identically or differently a hydrogen atom, a C1-C6 alkoxy group, a C1-C6 alkyl group or a C6-C14 aromatic hydrocarbon group, or $R_2$ and $R_3$ may form, together with a nitrogen atom that binds thereto, a saturated nitrogen-containing 4-8-membered heterocyclic group which may be substituted with a hydroxyl group; and
$R_4$, $R_5$ and $R_6$ are identically or differently a hydrogen atom or a C1-C6 alkyl group which may be substituted with a di(C1-C6 alkyl)amino group.

[3] The therapeutic agent according to [1] or [2], wherein the pyrazolo[3,4-d]pyrimidine compound is a compound represented by General formula (I), wherein:
X is a pyrrolidinyl group, a methylpyrrolidinyl group, a piperidinyl group or a fluoropiperidinyl group;
Y is:

[Chemical formula 2]

$Z_1$, $Z_2$, $Z_3$ and $Z_4$ are identically or differently a hydrogen atom, a fluorine atom, a chlorine atom, a bromine atom, a cyano group, a vinyl group, a methoxy group, a fluoromethoxy group, a difluoromethoxy group, a methyl group, an ethyl group, a dimethylamino group, a cyclopropyl group or a furyl group, or $Z_1$ and $Z_2$ or $Z_3$ and $Z_4$ may form, together with carbon atoms that bind thereto, a benzene ring, a pyridine ring or a dioxolane ring;
W is —CH$_2$—, an oxygen atom or —NH—;
n is 0;
$R_1$ is an amino group;
$R_2$ and $R_3$ are identically or differently a methoxy group, a methyl group or a phenyl group, or $R_2$ and $R_3$ may form, together with a nitrogen atom that binds thereto, a hydroxyazetidinyl group, a pyrrolidinyl group or a piperidinyl group.

[4] The therapeutic agent according to any one of [1]-[3], wherein the pyrazolo[3,4-d]pyrimidine compound is a compound selected from (1)-(20) below:
(1) (R)-1-(1-acryloylpiperidine-3-yl)-4-amino-N-(5-bromo-4-(2-(dimethylamino)-2-oxoethyl)-2-methylphenyl)-1H-pyrazolo[3,4-d]pyrimidine-3-carboxamide;
(2) (R)-1-(1-acryloylpiperidine-3-yl)-4-amino-N-(2-chloro-4-(2-(dimethylamino)-2-oxoethyl)-5-methylphenyl)-1H-pyrazolo[3,4-d]pyrimidine-3-carboxamide;
(3) (R)-1-(1-acryloylpiperidine-3-yl)-4-amino-N-(2-chloro-4-(2-(dimethylamino)-2-oxoethyl)-3-methylphenyl)-1H-pyrazolo[3,4-d]pyrimidine-3-carboxamide;
(4) (R)-1-(1-acryloylpiperidine-3-yl)-4-amino-N-(4-(2-(dimethylamino)-2-oxoethyl)-2-methylphenyl)-1H-pyrazolo[3,4-d]pyrimidine-3-carboxamide;
(5) (R)-1-(1-acryloylpiperidine-3-yl)-4-amino-N-(4-(2-(dimethylamino)-2-oxoethyl)naphthalene-1-yl)-1H-pyrazolo[3,4-d]pyrimidine-3-carboxamide;
(6) (R)-1-(1-acryloylpiperidine-3-yl)-4-amino-N-(2-chloro-4-(2-(dimethylamino)-2-oxoethyl)phenyl)-1H-pyrazolo[3,4-d]pyrimidine-3-carboxamide;
(7) (R)-1-(1-acryloylpiperidine-3-yl)-4-amino-N-(4-(2-(dimethylamino)-2-oxoethyl)-2-methoxyphenyl)-1H-pyrazolo[3,4-d]pyrimidine-3-carboxamide;
(8) (R)-1-(1-acryloylpiperidine-3-yl)-4-amino-N-(3-chloro-4-(2-(dimethylamino)-2-oxoethyl)phenyl)-1H-pyrazolo[3,4-d]pyrimidine-3-carboxamide;
(9) (R)-1-(1-acryloylpiperidine-3-yl)-4-amino-N-(5-chloro-4-(2-(dimethylamino)-2-oxoethyl)-2-methoxyphenyl)-1H-pyrazolo[3,4-d]pyrimidine-3-carboxamide;
(10) (R)-1-(1-acryloylpiperidine-3-yl)-4-amino-N-(4-(2-(dimethylamino)-2-oxoethyl)-5-fluoro-2-methylphenyl)-1H-pyrazolo[3,4-d]pyrimidine-3-carboxamide;
(11) (R)-1-(1-acryloylpiperidine-3-yl)-4-amino-N-(3-chloro-4-(2-(dimethylamino)-2-oxoethyl)-2-methoxyphenyl)-1H-pyrazolo[3,4-d]pyrimidine-3-carboxamide;
(12) (R)-1-(1-acryloylpiperidine-3-yl)-4-amino-N-(4-(2-(dimethylamino)-2-oxoethyl)-3-fluoro-2-methylphenyl)-1H-pyrazolo[3,4-d]pyrimidine-3-carboxamide;
(13) (R)-1-(1-acryloylpiperidine-3-yl)-4-amino-N-(4-(2-(dimethylamino)-2-oxoethyl)-2,3-dimethylphenyl)-1H-pyrazolo[3,4-d]pyrimidine-3-carboxamide;
(14) (R)-1-(1-acryloylpiperidine-3-yl)-4-amino-N-(4-(2-(dimethylamino)-2-oxoethyl)-3-fluoro-2-methoxyphenyl)-1H-pyrazolo[3,4-d]pyrimidine-3-carboxamide;
(15) (R)-1-(1-acryloylpiperidine-3-yl)-4-amino-N-(2-(difluoromethoxy)-4-(2-(dimethylamino)-2-oxoethyl)phenyl)-1H-pyrazolo[3,4-d]pyrimidine-3-carboxamide;
(16) (R)-1-(1-acryloylpiperidine-3-yl)-4-amino-N-(4-(2-(dimethylamino)-2-oxoethyl)-2-(fluoromethoxy)phenyl)-1H-pyrazolo[3,4-d]pyrimidine-3-carboxamide;
(17) (R)-1-(1-acryloylpiperidine-3-yl)-4-amino-N-(2-bromo-4-(2-(dimethylamino)-2-oxoethyl)phenyl)-1H-pyrazolo[3,4-d]pyrimidine-3-carboxamide;
(18) (R)-1-(1-acryloylpiperidine-3-yl)-4-amino-N-(2-chloro-4-(2-(dimethylamino)-2-oxoethyl)-5-fluorophenyl)-1H-pyrazolo[3,4-d]pyrimidine-3-carboxamide;
(19) (R)-1-(1-acryloylpiperidine-3-yl)-4-amino-N-(5-chloro-4-(2-(dimethylamino)-2-oxoethyl)-2-methylphenyl)-1H-pyrazolo[3,4-d]pyrimidine-3-carboxamide; and
(20) (R)-1-(1-acryloylpiperidine-3-yl)-4-amino-N-(2,5-dichloro-4-(2-(dimethylamino)-2-oxoethyl)phenyl)-1H-pyrazolo[3,4-d]pyrimidine-3-carboxamide.

[5] The therapeutic agent according to any one of [1]-[4], wherein the pyrazolo[3,4-d]pyrimidine compound is (R)-1-(1-acryloylpiperidine-3-yl)-4-amino-N-(4-(2-(dimethylamino)-2-oxoethyl)-2,3-dimethylphenyl)-1H-pyrazolo[3,4-d]pyrimidine-3-carboxamide.

[6] The therapeutic agent according to any one of [1]-[5], wherein the resistance or intractability to other antitumor agents is resistance or intractability that is acquired via a treatment with a HER2 inhibitor.

[7] The therapeutic agent according to any one of [1]-[5], wherein the resistance or intractability to other antitumor agents is intrinsic resistance or intractability irrelevant to a treatment with a HER2 inhibitor.

[8] The therapeutic agent according to [6] or [7], wherein the HER2 inhibitor is an anti-HER2 antibody.

[9] The therapeutic agent according to [8], wherein the anti-HER2 antibody is at least one selected from the group consisting of trastuzumab, trastuzumab emtansine and pertuzumab.

Other embodiments of the present invention also relate to the following aspects.

[10] A pharmaceutical composition for use in the treatment of a HER2-positive tumor which is resistant or intractable to other antitumor agents, the pharmaceutical composition comprising a pyrazolo[3,4-d]pyrimidine compound represented by General formula (I) above or a salt thereof as an active ingredient.

[11] Use of a pyrazolo[3,4-d]pyrimidine compound represented by General formula (I) above or a salt thereof for the production of a therapeutic agent for a HER2-positive tumor that is resistant or intractable to other antitumor agents.

[12] A method for the treatment of a HER2-positive tumor which is resistant or intractable to other antitumor agents, the method comprising a step of administering an effective amount of a pyrazolo[3,4-d]pyrimidine compound represented by General formula (I) above or a salt thereof.

Effect of the Invention

The present invention can realize a cancer treatment with a superior anti-tumor effect on a HER2-positive tumor which is resistant or intractable to other antitumor agents.

MODES FOR CARRYING OUT THE INVENTION

The present inventors have gone through extensive studies and as a result of which found that a compound represented by Formula (I) below which is based on pyrazolo[3,4-d]pyrimidine, or a salt thereof, exhibits a superior anti-tumor effect on a HER2-positive tumor which is resistant or intractable to other antitumor agents, thereby accomplishing the present invention.

According to the present invention, a compound that shows a superior anti-tumor effect on a HER2-positive tumor which is resistant or intractable to other antitumor agents is a pyrazolo[3,4-d]pyrimidine compound represented by General formula (I) below or a salt thereof.

[Chemical formula 3]

(wherein, X, Y, $Z_1$-$Z_4$, W, n and $R_1$-$R_3$ are as defined above).

Herein, examples of the "substituent" include a halogen atom, a hydroxyl group, a cyano group, a nitro group, an alkyl group, a halogenoalkyl group, a cycloalkyl group, a cycloalkyl-alkyl group, an aralkyl group, an alkenyl group, an alkynyl group, an alkoxy group, a halogenoalkoxy group, a cycloalkoxy group, a cycloalkyl-alkoxy group, an aralkyloxy group, an alkylthio group, a cycloalkyl-alkylthio group, an amino group, a mono- or di-alkylamino group, a cycloalkyl-alkylamino group, an acyl group, an acyloxy group, an oxo group, a carboxyl group, an alkoxycarbonyl group, an aralkyloxycarbonyl group, a carbamoyl group, a saturated or unsaturated heterocyclic group, an aromatic hydrocarbon group and a saturated heterocyclic oxy group, where if said substituent is present, the number thereof is typically 1, 2 or 3.

Herein, examples of the "halogen atom" include a fluorine atom, a chlorine atom, a bromine atom and an iodine atom.

Herein, the "alkyl group" may be either linear or branched, and examples thereof include C1-C6 alkyl groups such as a methyl group, an ethyl group, a n-propyl group, an isopropyl group, a n-butyl group, an isobutyl group, a sec-butyl group, a tert-butyl group, a n-pentyl group, an isopentyl group and a hexyl group.

Herein, the "halogenoalkyl group" is a linear or branched C1-C6 alkyl group which has 1 to 13 halogen atoms (C1-C6 halogenoalkyl group), and examples thereof include C1-C6 halogenoalkyl groups such as a fluoromethyl group, a difluoromethyl group, a trifluoromethyl group, a trichloromethyl group, a fluoroethyl group, a 1,1,1-trifluoroethyl group, a monofluoro-n-propyl group, a perfluoro-n-propyl group and a perfluoroisopropyl group, and preferably C1-C4 halogenoalkyl groups.

Herein, examples of the "cycloalkyl group" specifically include C3-C7 cycloalkyl groups such as a cyclopropyl group, a cyclobutyl group, a cyclopentyl group, a cyclohexyl group and a cycloheptyl group.

Herein, examples of the "cycloalkyl-alkyl group" include C3-C7 cycloalkyl-substituted C1-C4 alkyl groups such as a cyclopropylmethyl group, a cyclobutylmethyl group, a cyclopentylmethyl group, a cyclohexylmethyl group and a cycloheptylmethyl group.

Herein, examples of the "aralkyl group" include C7-C13 aralkyl groups such as a benzyl group, a phenethyl group, a naphtylmethyl group and a fluorenylmethyl group.

Herein, the "alkenyl group" may be linear, branched or cyclic, and refers to an unsaturated hydrocarbon group which has at least one double bond, for example, a C2-C6 alkenyl group such as a vinyl group, an allyl group, a 1-propenyl group, a 2-methyl-2-propenyl group, an isopropenyl group, a 1-, 2- or 3-butenyl group, a 2-, 3- or 4-pentenyl group, a 2-methyl-2-butenyl group, a 3-methyl-2-butenyl group, a 5-hexenyl group, a 1-cyclopentenyl group, a 1-cyclohexenyl group and a 3-methyl-3-butenyl group.

Herein, the "alkynyl group" may be linear, branched or cyclic, and refers to an unsaturated hydrocarbon group having at least one triple bond, for example, a C2-C6 alkynyl group such as an ethynyl group, a 1- or 2-propynyl group, a 1-, 2- or 3-butynyl group and a 1-methyl-2-propynyl group.

Herein, the "alkoxy group" may be either linear or branched, and examples thereof include C1-C6 alkoxy groups such as a methoxy group, an ethoxy group, a n-propoxy group, an isopropoxy group, a n-butoxy group, an isobutoxy group, a sec-butoxy group, a tert-butoxy group, a pentyloxy group, an isopentyloxy group and a hexyloxy group.

Herein, the "halogenoalkoxy group" is a linear or branched C1-C6 alkoxy group which has 1 to 13 halogen atoms (C1-C6 halogenoalkoxy group), and examples thereof include C1-C6 halogenoalkoxy groups such as a fluoromethoxy group, a difluoromethoxy group, a trifluoromethoxy group, a trichloromethoxy group, a fluoroethoxy group, a 1,1,1-trifluoroethoxy group, a monofluoro-n-propoxy group, a perfluoro-n-propoxy group and a perfluoro-isopropoxy group, preferably a C1-C4 halogenoalkoxy group.

Herein, examples of the "cycloalkoxy group" include C3-C7 cycloalkoxy groups such as a cyclopropoxy group, a cyclobutoxy group, a cyclopentyloxy group, a cyclohexyloxy group and a cycloheptyloxy group.

Herein, examples of the "cycloalkyl-alkoxy group" include C3-C7 cycloalkyl-substituted C1-C4 alkoxy groups such as a cyclopropylmethoxy group, a cyclobutylmethoxy group, a cyclopentylmethoxy group, a cyclohexylmethoxy group and a cycloheptylmethoxy group.

Herein, examples of the "aralkyloxy group" include C7-C13 aralkyloxy groups such as a benzyloxy group, a phenethyloxy group, a naphthylmethyloxy group and a fluorenylmethyloxy group.

Herein, the "alkylthio" may be either linear or branched, and examples thereof include C1-C6 alkylthio groups such as a methylthio group, an ethylthio group, a n-propylthio group, an isopropylthio group, a n-butylthio group, an isobutylthio group, a tert-butylthio group, a n-pentylthio group, an isopentylthio group and a hexylthio group.

Herein, examples of the "cycloalkyl-alkylthio group" include C3-C7 cycloalkyl-substituted C1-C4 alkylthio groups such as a cyclopropylmethylthio group, a cyclobutylmethylthio group, a cyclopentylmethylthio group, a cyclohexylmethylthio group and a cycloheptylmethylthio group.

Herein, examples of the "monoalkylamino group" include amino groups which are mono-substituted with a linear or branched C1-C6 alkyl group such as a methylamino group, an ethylamino group, a n-propylamino group, an isopropylamino group, a n-butylamino group, an isobutylamino group, a tert-butylamino group, a n-pentylamino group, an isopentylamino group and a hexylamino group.

Herein, examples of the "dialkylamino group" include amino groups which are di-substituted with a linear or branched C1-C6 alkyl group such as a dimethylamino group, a diethylamino group, a di(n-propyl)amino group, a diisopropylamino group, a di(n-butyl)amino group, a diisobutylamino group, a di(tert-butyl)amino group, a di(n-pentyl)amino group, a diisopentylamino group, a dihexylamino group, a methylethylamino group and a methylisopropylamino group.

Herein, examples of the "cycloalkyl-alkylamino group" include C3-C7 cycloalkyl-substituted C1-C4 alkylamino groups such as a cyclopropylmethylamino group, a cyclobutylmethylamino group, a cyclopentylmethylamino group, a cyclohexylmethylamino group and a cycloheptylmethylamino group.

Herein, the "acyl group" refers to an alkylcarbonyl group or an arylcarbonyl group.

Herein, examples of the "alkylcarbonyl group" include linear or branched (C1-C6 alkyl)carbonyl groups such as a methylcarbonyl group, an ethylcarbonyl group, a n-propylcarbonyl group, an isopropylcarbonyl group, a n-butylcarbonyl group, an isobutylcarbonyl group, a tert-butylcarbonyl group, a n-pentylcarbonyl group, an isopentylcarbonyl group and a hexylcarbonyl group.

Herein, examples of the "arylcarbonyl group" include (C6-C13 aryl)carbonyl groups such as a phenylcarbonyl group, a naphthylcarbonyl group, a fluorenylcarbonyl group, an anthrylcarbonyl group, a biphenylcarbonyl group, a tetrahydronaphthylcarbonyl group, a chromanylcarbonyl group, a 2,3-dihydro-1,4-dioxanaphthalenylcarbonyl group, an indanylcarbonyl group and a phenanthrylcarbonyl group.

Herein, the "acyloxy group" refers to an alkylcarbonyloxy group or an arylcarbonyloxy group.

Herein, examples of the "alkylcarbonyloxy group" include linear or branched (C1-C6 alkyl)carbonyloxy groups such as a methylcarbonyloxy group, an ethylcarbonyloxy group, a n-propylcarbonyloxy group, an isopropylcarbonyloxy group, a n-butylcarbonyloxy group, an isobutylcarbonyloxy group, a tert-butylcarbonyloxy group, a n-pentylcarbonyloxy group, an isopentylcarbonyloxy group and a hexylcarbonyloxy group.

Herein, examples of the "arylcarbonyloxy group" include (C6-C13 aryl)carbonyloxy groups such as a phenylcarbonyloxy group, a naphthylcarbonyloxy group, a fluorenylcarbonyloxy group, an anthrylcarbonyloxy group, a biphenylcarbonyloxy group, a tetrahydronaphthylcarbonyloxy group, a chromanylcarbonyloxy group, a 2,3-dihydro-1,4-dioxanaphthalenylcarbonyloxy group, an indanylcarbonyloxy group and a phenanthrylcarbonyloxy group.

Herein, the "alkoxycarbonyl group" may be either linear or branched, and examples thereof include (C1-C6 alkoxy)carbonyl groups such as a methoxycarbonyl group, an ethoxycarbonyl group, a propoxycarbonyl group, an isopropoxycarbonyl group, a butoxycarbonyl group, an isobutoxycarbonyl group, a tert-butoxycarbonyl group, a pentyloxycarbonyl group, an isopentyloxycarbonyl group and a hexyloxycarbonyl group.

Herein, examples of the "aralkyloxycarbonyl group" include (C7-C13 aralkyl)oxycarbonyl groups such as a benzyloxycarbonyl group, a phenethyloxycarbonyl group, a naphthylmethyloxycarbonyl group and a fluorenylmethyloxycarbonyl group.

Herein, the "saturated heterocyclic group" refers to a saturated heterocyclic group that has a hetero atom selected from a nitrogen atom, an oxygen atom and a sulfur atom, and examples thereof specifically include a morpholino group, a pyrrolidinyl group, a piperidinyl group, a piperazinyl group, a 4-methyl-1-piperazinyl group, a tetrahydrofuranyl group, a tetrahydropyranyl group, a tetrahydrothiophenyl group, a thiazolidinyl group and an oxazolidinyl group.

Herein, the "unsaturated heterocyclic group" refers to a completely unsaturated or partially unsaturated heteromonocyclic or heteropolycyclic group which has a hetero atom selected from a nitrogen atom, an oxygen atom and a sulfur atom, and examples thereof specifically include an imidazolyl group, a thienyl group, a furyl group, a pyrrolyl group, an oxazolyl group, an isoxazolyl group, a thiazolyl group, an isothiazolyl group, a thiadiazolyl group, a pyrazolyl group, a triazolyl group, a tetrazolyl group, a pyridyl group, a pyrazyl group, a pyrimidinyl group, a pyridazinyl group, an indolyl group, an isoindolyl group, an indazolyl group, a triazolopyridyl group, a benzoimidazolyl group, a benzoxazolyl group, a benzothiazolyl group, a benzothienyl group, a benzofuranyl group, a purinyl group, a quinolyl group, an isoquinolyl group, a quinazolinyl group, a quinoxalyl group, a methylenedioxyphenyl group, an ethylenedioxyphenyl group and a dihydrobenzofuranyl group.

Herein, examples of the "aromatic hydrocarbon group" include C6-C14 aromatic hydrocarbon groups such as a phenyl group, a tolyl group, a xylyl group, a naphthyl group, an anthracenyl group, a phenanthryl group, a fluorenyl group and a tetrahydronaphthyl group.

Herein, the "saturated heterocyclic oxy group" refers to a saturated heterocyclic oxy group having a hetero atom selected from a nitrogen atom, an oxygen atom and a sulfur atom, and examples thereof specifically include a morpholinyloxy group, a 1-pyrrolidinyloxy group, a piperidinoxy group, a piperazinyloxy group, a 4-methyl-1-piperazinyloxy group, a tetrahydrofuranyloxy group, a tetrahydropyranyloxy group, a tetrahydrothiophenyloxy group, a thiazolidinyloxy group and an oxazolidinyloxy group.

As to the groups referred to herein, "CA-CB" means that it is a group with a carbon number of A-B. For example, a "C1-C6 alkyl group" refers to an alkyl group with a carbon number of 1-6, and a "C6-C14 aromatic hydrocarbonoxy group" refers to an oxy group attached to an aromatic hydrocarbon group with a carbon number of 6-14. Furthermore "A-B-membered" means that the number of atoms (number of members) forming a ring is A-B. For example, a "saturated 4-10-membered heterocyclic group" refers to a saturated heterocyclic group with a number of members of 4-10.

In a pyrazolo[3,4-d]pyrimidine compound represented by General formula (I) used in the present invention, X represents a saturated, optionally substituted nitrogen-containing 4-10-membered heterocyclic group. Here, the "saturated nitrogen-containing 4-10-membered heterocyclic group" refers to a saturated 4-10-membered heterocyclic group which contains at least one nitrogen atom in the ring, and further contains zero to two identical or different kinds of hetero atoms selected from an oxygen atom and a sulfur atom in the ring. Examples of such groups include an azetidinyl group, a pyrrolidinyl group, a piperidinyl group, a piperazinyl group, a morpholinyl group, an octahydroquinolinylene group and an octahydroindolylene group.

X is preferably a saturated 4-8-membered heterocyclic group containing one nitrogen atom in the ring, more preferably a pyrrolidinyl group or a piperidinyl group, still more preferably a 1,3-pyrrolidinyl group or a 1,3-piperidinyl group, and yet still more preferably a 1,3-piperidinyl group.

While a "substituent" that may be used for substitution in these saturated nitrogen-containing 4-10-membered heterocyclic groups may typically be a substituent mentioned above, it is preferably a halogen atom, a hydroxyl group, a cyano group, a C1-C6 alkyl group or an amino group, more preferably a halogen atom or a C1-C6 alkyl group, still more preferably a fluorine atom or a methyl group, and yet still more preferably a fluorine atom.

The saturated nitrogen-containing 4-10-membered heterocyclic group that may be substituted with a halogen atom or a C1-C6 alkyl group is preferably a pyrrolidinyl group that may be substituted with a halogen atom or a C1-C6 alkyl group or a piperidinyl group that may be substituted with a halogen atom or a C1-C6 alkyl group, more preferably a pyrrolidinyl group that may be substituted with a C1-C6 alkyl group or a piperidinyl group that may be substituted with a fluorine atom, still more preferably a pyrrolidinyl group, a methylpyrrolidinyl group, a piperidinyl group or a fluoropiperidinyl group, and yet still more preferably a piperidinyl group or a fluoropiperidinyl group.

X in a pyrazolo[3,4-d]pyrimidine compound represented by General formula (I) is preferably a saturated, optionally substituted nitrogen-containing 4-10-membered heterocyclic group, more preferably a saturated nitrogen-containing 4-10-membered heterocyclic group which may have a halogen atom, a hydroxyl group, a cyano group, a C1-C6 alkyl group or an amino group as a substituent, more preferably a saturated nitrogen-containing 4-8-membered heterocyclic group which may have a halogen atom or a C1-C6 alkyl group as a substituent, more preferably a pyrrolidinyl group which may have a halogen atom or a C1-C6 alkyl group as a substituent or a piperidinyl group which may have a halogen atom or a C1-C6 alkyl group as a substituent, more preferably a pyrrolidinyl group which may have a C1-C6 alkyl group as a substituent or a piperidinyl group which may have a halogen atom as a substituent, more preferably a pyrrolidinyl group which may have a methyl group as a substituent or a piperidinyl group which may have a fluorine atom as a substituent, still more preferably a piperidinyl group which may have a fluorine atom as a substituent, and yet still more preferably a piperidinyl group.

The nitrogen atom of the saturated nitrogen-containing 4-10-membered heterocyclic group represented by X is preferably attached to the carbonyl group of —COY in General formula (I).

In the pyrazolo[3,4-d]pyrimidine compound represented by General formula (I) used in the present invention, Y represents —C($R_4$)=C($R_5$)($R_6$). Details of $R_4$, $R_5$ and R will be described later.

In the pyrazolo[3,4-d]pyrimidine compound represented by General formula (I) used in the present invention, $Z_1$, $Z_2$, $Z_3$ and $Z_4$ identically or differently represent a hydrogen atom, a halogen atom, a cyano group, a C2-C6 alkenyl group, an optionally substituted C1-C6 alkoxy group, an optionally substituted C1-C6 alkyl group, an optionally substituted amino group, an optionally substituted C3-C7 cycloalkyl group, a C6-C14 aromatic hydrocarbon group or an unsaturated 4-14-membered heterocyclic group, or $Z_1$ and $Z_2$ or $Z_3$ and $Z_4$ may form, together with carbon atoms that bind thereto, a benzene ring or a saturated or unsaturated 5-7-membered heterocycle.

The "C2-C6 alkenyl group" represented by $Z_1$, $Z_2$, $Z_3$ or $Z_4$ is preferably a vinyl group, a propenyl group, a butenyl group, a pentenyl group, a hexenyl group, a cyclopropenyl group, a cyclobutenyl group, a cyclopentenyl group or a cyclohexenyl group, more preferably a vinyl group, a propenyl group, a butenyl group, a cyclopropenyl group or a cyclobutenyl group, still more preferably a vinyl group, a 1-propenyl group, a 2-propenyl group or an isopropenyl group, and yet still more preferably a vinyl group.

The "C1-C6 alkoxy group" in the "optionally substituted C1-C6 alkoxy group" represented by $Z_1$, $Z_2$, $Z_3$ or $Z_4$ is preferably a methoxy group, an ethoxy group, a propoxy group, a butoxy group, a pentyloxy group or a hexyloxy group, more preferably a methoxy group, an ethoxy group, a propoxy group or a butoxy group, still more preferably a methoxy group, an ethoxy group, a n-propoxy group, an isopropoxy group, a n-butoxy group, a sec-butoxy group or a tert-butoxy group, and yet still more preferably a methoxy group.

While the "substituent" in the "optionally substituted C1-C6 alkoxy group" represented by $Z_1$, $Z_2$, $Z_3$ or $Z_4$ may typically be a substituent mentioned above, it is preferably a halogen atom and more preferably a fluorine atom.

The "optionally substituted C1-C6 alkoxy group" represented by $Z_1$, $Z_2$, $Z_3$ or $Z_4$ is preferably a C1-C6 alkoxy group which may be substituted with a halogen atom, more preferably a C1-C6 alkoxy group which may be substituted with a fluorine atom, more preferably a methoxy group which may be substituted with a fluorine atom, an ethoxy group which may be substituted with a fluorine atom, a propoxy group which may be substituted with a fluorine atom, a butoxy group which may be substituted with a fluorine atom, a pentyloxy group which may be substituted with a fluorine atom or a hexyloxy group which may be substituted with a fluorine atom, more preferably a methoxy group which may be substituted with a fluorine atom, an ethoxy group which may be substituted with a fluorine atom, a propoxy group which may be substituted with a fluorine atom or a butoxy group which may be substituted with a fluorine atom, still more preferably a methoxy group which may be substituted with a fluorine atom, an ethoxy group which may be substituted with a fluorine atom, a n-propoxy group which may be substituted with a fluorine atom, an isopropoxy group which may be substituted with a fluorine atom, a n-butoxy group which may be substituted with a fluorine atom, a sec-butoxy group which may be substituted with a fluorine atom or a tert-butoxy group which may be substituted with a fluorine atom, yet still more preferably a methoxy group which may be substituted with one or two fluorine atoms, an ethoxy group which may be substituted with one or two fluorine atoms, a n-propoxy group which may be substituted with one or two fluorine atoms, an isopropoxy group which may be substituted with one or two fluorine atoms, a n-butoxy group which may be substituted with one or two fluorine atoms, a sec-butoxy group which may be substituted with one or two fluorine atoms or a tert-butoxy group which may be substituted with one or two fluorine atoms, and particularly preferably a methoxy group, a fluoromethoxy group or a difluoromethoxy group.

The "C1-C6 alkyl group" of the "optionally substituted C1-C6 alkyl group" represented by $Z_1$, $Z_2$, $Z_3$ or $Z_4$ is preferably a methyl group, an ethyl group, a propyl group, a butyl group, a pentyl group or a hexyl group, more preferably a methyl group, an ethyl group, a n-propyl group, an isopropyl group, a n-butyl group, an isobutyl group, a sec-butyl group or a tert-butyl group, and still more preferably a methyl group or an ethyl group.

The "substituent" in the "optionally substituted C1-C6 alkyl group" represented by $Z_1$, $Z_2$, $Z_3$ or $Z_4$ may typically be a substituent mentioned above.

The "optionally substituted C1-C6 alkyl group" represented by $Z_1$, $Z_2$, $Z_3$ or $Z_4$ is preferably an unsubstituted C1-C6 alkyl group, more preferably a methyl group, an ethyl group, a propyl group, a butyl group, a pentyl group or a hexyl group, still more preferably a methyl group, an ethyl group, a n-propyl group, an isopropyl group, a n-butyl group, an isobutyl group, a sec-butyl group or a tert-butyl group, and particularly preferably a methyl group or an ethyl group.

The "substituent" of the "optionally substituted amino group" represented by $Z_1$, $Z_2$, $Z_3$ or $Z_4$ may typically be a substituent mentioned above, preferably an alkyl group, more preferably a C1-C6 alkyl group, more preferably a methyl group, an ethyl group, a propyl group, a butyl group, a pentyl group or a hexyl group, still more preferably a methyl group, an ethyl group, a n-propyl group, an isopropyl group, n-butyl group, an isobutyl group, a sec-butyl group or a tert-butyl group, and particularly preferably a methyl group.

The optionally substituted amino group represented by $Z_1$, $Z_2$, $Z_3$ or $Z_4$ is preferably a mono- or di-alkylamino group, more preferably a mono- or di-(C1-C6 alkyl)amino group, more preferably a di(C1-C6 alkyl)amino group, more preferably a di(C1-C4 alkyl)amino group, and still more preferably a dimethylamino group.

The "C3-C7 cycloalkyl group" in the "optionally substituted C3-C7 cycloalkyl group" represented by $Z_1$, $Z_2$, $Z_3$ or $Z_4$ is preferably a cyclopropyl group, a cyclobutyl group, a cyclopentyl group, a cyclohexyl group or a cycloheptyl group, more preferably a cyclopropyl group, a cyclobutyl group, a cyclopentyl group or a cyclohexyl group, and still more preferably a cyclopropyl group.

The "substituent" in the "optionally substituted C3-C7 cycloalkyl group" represented by $Z_1$, $Z_2$, $Z_3$ or $Z_4$ may typically be a substituent mentioned above.

The "optionally substituted C3-C7 cycloalkyl group" represented by $Z_1$, $Z_2$, $Z_3$ or $Z_4$ is preferably an unsubstituted C3-C7 cycloalkyl group, more preferably a cyclopropyl group, a cyclobutyl group, a cyclopentyl group, a cyclohexyl group or a cycloheptyl group, still more preferably a cyclopropyl group, a cyclobutyl group, a cyclopentyl group or a cyclohexyl group, and particularly preferably a cyclopropyl group.

The "C6-C14 aromatic hydrocarbon group" represented by $Z_1$, $Z_2$, $Z_3$ or $Z_4$ is preferably a phenyl group or a naphthyl group, and more preferably a phenyl group.

The "unsaturated heterocyclic group" represented by $Z_1$, $Z_2$, $Z_3$ or $Z_4$ is a completely unsaturated or partially unsaturated heteromonocyclic or heteropolycyclic group which has a hetero atom selected from a nitrogen atom, an oxygen atom and a sulfur atom, and examples thereof include an imidazolyl group, a thienyl group, a furyl group, a pyrrolyl group, an oxazolyl group, an isoxazolyl group, a thiazolyl group, an isothiazolyl group, a thiadiazolyl group, a pyrazolyl group, a triazolyl group, a tetrazolyl group, a pyridyl group, a pyrazyl group, a pyrimidinyl group, a pyridazinyl group, an indolyl group, an isoindolyl group, an indazolyl group, a triazolopyridyl group, a benzoimidazolyl group, a benzoxazolyl group, a benzothiazolyl group, a benzothienyl group, a benzofuranyl group, a purinyl group, a quinolyl group, an isoquinolyl group, a quinazolinyl group, a quinoxalyl group, a methylenedioxyphenyl group, an ethylenedioxyphenyl group and a dihydrobenzofuranyl group, and is preferably an unsaturated 4-14-membered heteromonocyclic or heterobicyclic group which has one hetero atom selected from a nitrogen atom, an oxygen atom or a sulfur atom, more preferably a completely unsaturated 4-6-membered heteromonocyclic group which has one hetero atom selected from a nitrogen atom, an oxygen atom or a sulfur atom, still more preferably a completely unsaturated 4-6- membered heteromonocyclic group which has one oxygen atom, and yet still more preferably a furyl group.

The "saturated or unsaturated 5-7-membered heterocycle" formed by $Z_1$ and $Z_2$ or $Z_3$ and $Z_4$ together with carbon atoms that bind thereto is a saturated, completely unsaturated or partially unsaturated 5-7-membered heterocycle which has a hetero atom selected from a nitrogen atom, an oxygen atom or a sulfur atom.

The number of hetero atoms in the ring is preferably 0-2, and more preferably 1-2. The hetero atom is preferably a nitrogen atom or an oxygen atom.

The saturated or unsaturated 5-7-membered heterocycle is preferably a pyrrole ring, a pyrazole ring, an imidazole ring, a pyridine ring, a pyrazine ring, a pyrimidine ring or a dioxolane ring, and more preferably a pyridine ring or a dioxolane ring.

A benzene ring is also preferable as the ring formed by $Z_1$ and $Z_2$ or $Z_3$ and $Z_4$ together with carbon atoms that bind thereto.

$Z_1$, $Z_2$, $Z_3$ and $Z_4$ in the pyrazolo[3,4-d]pyrimidine compound represented by General formula (I): preferably identically or differently represent a hydrogen atom, a halogen atom, a cyano group, a C2-C6 alkenyl group, an optionally substituted C1-C6 alkoxy group, an optionally substituted C1-C6 alkyl group, an optionally substituted amino group, an optionally substituted C3-C7 cycloalkyl group, a C6-C14 aromatic hydrocarbon group or an unsaturated 4-14-membered heteromonocyclic or heterobicyclic group, or $Z_1$ and $Z_2$ or $Z_3$ and $Z_4$ may form, together with carbon atoms that bind thereto, a benzene ring or a saturated or unsaturated 5-7-membered heterocycle; more preferably identically or differently represent a hydrogen atom, a halogen atom, a cyano group, a C2-C6 alkenyl group, an optionally substituted C1-C6 alkoxy group, an optionally substituted C1-C6 alkyl group, an optionally substituted amino group, an optionally substituted C3-C7 cycloalkyl group or an unsaturated 4-14-membered heteromonocyclic or heterobicyclic group, or $Z_1$ and $Z_2$ or $Z_3$ and $Z_4$ may form, together with carbon atoms that bind thereto, a benzene ring or a saturated or unsaturated 5-7-membered heterocycle; more preferably identically or differently a hydrogen atom, a halogen atom, a cyano group, a C2-C6 alkenyl group, an optionally substituted C1-C6 alkoxy group, a C1-C6 alkyl group, an optionally substituted amino group, a C3-C7 cycloalkyl group or an unsaturated 4-6-membered heteromonocyclic group which has one hetero atom selected from a nitrogen atom, an oxygen atom or a sulfur atom, or $Z_1$ and $Z_2$ or $Z_3$ and $Z_4$ may form, together with carbon atoms that bind thereto, a benzene ring or a saturated or unsaturated 5-7-membered heterocycle; more preferably identically or differently represent a hydrogen atom, a halogen atom, a cyano group, a C2-C6 alkenyl group, a C1-C6 alkoxy group which may be substituted with a halogen atom, a C1-C6 alkyl group, an amino group which may be substituted with a C1-C6 alkyl group, a C3-C7 cycloalkyl group or an unsaturated 4-6-membered heteromonocyclic group which has one hetero atom selected from a nitrogen atom, an oxygen atom or a sulfur atom, or $Z_1$ and $Z_2$ or $Z_3$ and $Z_4$ may form, together with carbon atoms that bind thereto, a benzene ring or a saturated or unsaturated 5-7-membered heterocycle; more preferably identically or differently represent a hydrogen atom, a fluorine atom, a chlorine atom, a bromine atom, a cyano group, a C2-C6 alkenyl group, a C1-C6 alkoxy group which may be substituted with a fluorine atom, a C1-C6 alkyl group, a mono- or di-(C1-C6 alkyl)amino group, a C3-C7 cycloalkyl group or an unsaturated 4-6-membered heteromonocyclic group having one oxygen atom, or $Z_1$ and $Z_2$ or $Z_3$ and $Z_4$ may form, together with carbon atoms that bind thereto, a benzene ring or a saturated or unsaturated 5-7-membered heterocycle; more preferably identically or differently represent a hydrogen atom, a fluorine atom, a chlorine atom, a bromine atom, a cyano group, a C2-C6 alkenyl group, a C1-C6 alkoxy group which may be substituted with one or two fluorine atoms, a C1-C6 alkyl group, a di(C1-C6 alkyl)amino group, a C3-C7 cycloalkyl group or an unsaturated 4-6-membered heteromonocyclic group having one oxygen atom, or $Z_1$ and $Z_2$ or $Z_3$ and $Z_4$ may form, together with carbon atoms that bind thereto, a benzene ring or a saturated or unsaturated 5-7-membered heterocycle; more preferably identically or differently represent a hydrogen atom, a fluorine atom, a chlorine atom, a bromine atom, a cyano group, a vinyl group, a methoxy group, a fluoromethoxy group, a difluoromethoxy group, a methyl group, an ethyl group, a dimethylamino group, a cyclopropyl group or a furyl group, or $Z_1$ and $Z_2$ or $Z_3$ and $Z_4$ may form, together with carbon atoms that bind thereto, a benzene ring, a pyridine ring or a dioxolane ring; and more preferably identically or differently represent a hydrogen atom, a fluorine atom, a chlorine atom, a bromine atom, a methoxy group, a fluoromethoxy group, a difluoromethoxy group or a methyl group, or $Z_1$ and $Z_2$ or $Z_3$ and $Z_4$ may form a benzene ring together with carbon atoms that bind thereto.

In the pyrazolo[3,4-d]pyrimidine compound represented by General formula (I) used in the present invention, W represents —$CH_2$—, an oxygen atom or —NH—. W is preferably —$CH_2$— or an oxygen atom, and more preferably —$CH_2$—.

In the pyrazolo[3,4-d]pyrimidine compound represented by Formula (1) used in the present invention, n represents an integer of 0-2. n is preferably 0 or 1, and more preferably 0.

In the pyrazolo[3,4-d]pyrimidine compound represented by General formula (I) used in the present invention, $R_1$ represents an optionally substituted amino group. Here, the "substituent" that may be used for substitution in the amino group may typically be a substituent mentioned above.

The optionally substituted amino group represented by $R_1$ is preferably an unsubstituted amino group.

In the pyrazolo[3,4-d]pyrimidine compound represented by General formula (I) used in the present invention, $R_2$ and $R_3$ identically or differently represent a hydrogen atom, an optionally substituted C1-C6 alkoxy group, an optionally substituted C1-C6 alkyl group or an optionally substituted C6-C14 aromatic hydrocarbon group, or $R_2$ and $R_3$ may form a saturated, optionally substituted nitrogen-containing 4-8-membered heterocyclic group together with a nitrogen atom that binds thereto.

The "C1-C6 alkoxy group" in the "optionally substituted C1-C6 alkoxy group" represented by $R_2$ or $R_3$ is preferably a methoxy group, an ethoxy group, a n-propoxy group, an isopropoxy group, a n-butoxy group, an isobutoxy group, a sec-butoxy group, a tert-butoxy group, a pentyloxy group or a hexyloxy group, more preferably a methoxy group, an ethoxy group, a n-propoxy group, an isopropoxy group, a n-butoxy group, an isobutoxy group, a sec-butoxy group or a tert-butoxy group, and still more preferably a methoxy group.

The "substituent" in the optionally substituted C1-C6 alkoxy group represented by $R_2$ or $R_3$ may typically be a substituent mentioned above.

The "optionally substituted C1-C6 alkoxy group" represented by $R_2$ or $R_3$ is preferably an unsubstituted C1-C6 alkoxy group, more preferably a methoxy group, an ethoxy group, a n-propoxy group, an isopropoxy group, a n-butoxy group, an isobutoxy group, a sec-butoxy group, a tert-butoxy group, a pentyloxy group or a hexyloxy group, still more preferably a methoxy group, an ethoxy group, a n-propoxy group, an isopropoxy group, a n-butoxy group, an isobutoxy group, a sec-butoxy group or a tert-butoxy group, and particularly preferably a methoxy group.

The "C1-C6 alkyl group" in the "optionally substituted C1-C6 alkyl group" represented by $R_2$ or $R_3$ is preferably a methyl group, an ethyl group, a n-propyl group, an isopropyl group, a n-butyl group, an isobutyl group, a sec-butyl group, a tert-butyl group, a pentyl group or a hexyl group, more preferably a methyl group, an ethyl group, a n-propyl group, an isopropyl group, a n-butyl group, an isobutyl group, a sec-butyl group or a tert-butyl group, and still more preferably a methyl group.

While the "substituent" in the "optionally substituted C1-C6 alkyl group" represented by $R_2$ or $R_3$ may typically be a substituent mentioned above, it is preferably a C1-C6 alkoxy group, preferably a methoxy group, an ethoxy group, a n-propoxy group, an isopropoxy group, a n-butoxy group, an isobutoxy group, a sec-butoxy group, a tert-butoxy group, a pentyloxy group or a hexyloxy group, more preferably a methoxy group, an ethoxy group, a n-propoxy group, an isopropoxy group, a n-butoxy group, an isobutoxy group, a sec-butoxy group or a tert-butoxy group, and still more preferably a methoxy group or an ethoxy group.

The "optionally substituted C1-C6 alkyl group" represented by $R_2$ or $R_3$ is preferably an unsubstituted C1-C6 alkyl group or a C1-C6 alkoxy group-substituted C1-C6 alkyl group, more preferably an unsubstituted C1-C6 alkyl group, more preferably a methyl group, an ethyl group, a n-propyl group, an isopropyl group, a n-butyl group, an isobutyl group, a sec-butyl group, a tert-butyl group, a pentyl group or a hexyl group.

While the number of substituents, if any, is not particularly limited, it is preferably 1 when the substituent is a C1-C6 alkoxy group.

The "C6-C14 aromatic hydrocarbon group" in the "optionally substituted C6-C14 aromatic hydrocarbon group" represented by $R_2$ or $R_3$ is preferably a phenyl group or a naphthyl group, and more preferably a phenyl group.

While the "substituent" in the "optionally substituted C6-C14 aromatic hydrocarbon group" represented by $R_2$ or $R_3$ may typically be a substituent mentioned above, it is preferably a halogen atom. The C6-C14 aromatic hydrocarbon group which may be substituted with a halogen atom is preferably a phenyl group which may be substituted with a fluorine atom or a chlorine atom, more preferably a phenyl group, a fluorophenyl group, a difluorophenyl group, a trifluorophenyl group, a chlorophenyl group, a dichlorophenyl group or a trichlorophenyl group, and more preferably a phenyl group.

The "saturated nitrogen-containing 4-8-membered heterocyclic group" in the "saturated, optionally substituted nitrogen-containing 4-8-membered heterocyclic group" formed by $R_2$ and $R_3$ together with a nitrogen atom that binds thereto is a saturated 4-8-membered heterocyclic group which contains at least one nitrogen atom in the ring, and further, zero to two identical or different kinds of hetero atoms selected from an oxygen atom and a sulfur atom in the ring.

The saturated nitrogen-containing 4-8-membered heterocyclic group is preferably a saturated 4-8-membered heterocyclic group which contains one nitrogen atom, and more preferably an azetidinyl group, a pyrrolidinyl group or a piperidinyl group.

While the "substituent" in the "saturated, optionally substituted nitrogen-containing 4-8-membered heterocyclic group" may typically be a substituent mentioned above, it is preferably a hydroxyl group.

The saturated, optionally substituted nitrogen-containing 4-8-membered heterocyclic group is preferably a saturated nitrogen-containing 4-8-membered heterocyclic group which may be substituted with a hydroxyl group, more preferably an azetidinyl group, a pyrrolidinyl group, a piperidinyl group, a hydroxyazetidinyl group, a hydroxypyrrolidinyl group or a hydroxypiperidinyl group, and more preferably a pyrrolidinyl group, a piperidinyl group or a hydroxyazetidinyl group.

$R_2$ and $R_3$ in the pyrazolo[3,4-d]pyrimidine compound represented by General formula (I): preferably identically or differently represent a hydrogen atom, an optionally substituted C1-C6 alkoxy group, an optionally substituted C1-C6 alkyl group or an optionally substituted C6-C14 aromatic hydrocarbon group, or $R_2$ and $R_3$ may form, together with a nitrogen atom that binds thereto, a saturated, optionally substituted nitrogen-containing 4-8-membered heterocyclic group; more preferably identically or differently represent a hydrogen atom, a C1-C6 alkoxy group, a C1-C6 alkyl group which may have a C1-C6 alkoxy group as a substituent or a C6-C14 aromatic hydrocarbon group which may have a halogen atom as a substituent, or $R_2$ and $R_3$ may form, together with a nitrogen atom that binds thereto, a saturated, optionally substituted nitrogen-containing 4-8-membered heterocyclic group; more preferably identically or differently represent a hydrogen atom, a C1-C6 alkoxy group, a C1-C6 alkyl group or a C6-C14 aromatic hydrocarbon group, or $R_2$ and $R_3$ may form, together with a nitrogen atom that binds thereto, a saturated nitrogen-containing 4-8-membered heterocyclic group which may have a hydroxyl group as a substituent; more preferably identically or differently represent a C1-C6 alkoxy group, a C1-C6 alkyl group or a C6-C14 aromatic hydrocarbon group, or $R_2$ and $R_3$ may form, together with a nitrogen atom that binds thereto, a saturated nitrogen-containing 4-8-membered heterocyclic group which may have a hydroxyl group as a substituent; more preferably identically or differently represent a methoxy group, a methyl group or a phenyl group, or $R_2$ and $R_3$ may form, together with a nitrogen atom that binds thereto, an azetidinyl group, a pyrrolidinyl group or a piperidinyl group, which may have a hydroxyl group as a substituent; more preferably identically or differently represent a methoxy group, a methyl group or a phenyl group, or $R_2$ and $R_3$ may form a hydroxyazetidinyl group, a pyrrolidinyl group or a piperidinyl group together with a nitrogen atom that binds thereto; and more preferably are methyl groups.

In the pyrazolo[3,4-d]pyrimidine compound represented by General formula (I) used in the present invention, $R_4$, $R_5$ and $R_6$ identically or differently represent a hydrogen atom or an optionally substituted C1-C6 alkyl group.

The "C1-C6 alkyl group" in the "optionally substituted C1-C6 alkyl group" represented by $R_4$, $R_5$ or $R_6$ is preferably a methyl group, an ethyl group, a n-propyl group, an isopropyl group, a n-butyl group, an isobutyl group, a sec-butyl group, a tert-butyl group, a pentyl group or a hexyl group, more preferably a methyl group, an ethyl group, a n-propyl group, an isopropyl group, a n-butyl group, an isobutyl group, a sec-butyl group or a tert-butyl group, still more preferably a methyl group, an ethyl group, a n-propyl group or an isopropyl group, and particularly preferably a methyl group.

While the "substituent" in the "optionally substituted C1-C6 alkyl group" represented by $R_4$, $R_5$ or $R_6$ may typically be a substituent mentioned above, it is preferably a dialkylamino group or a saturated heterocyclic group, more preferably a di(C1-C6 alkyl)amino group or a saturated 4-8-membered heterocyclic group having a nitrogen atom, more preferably a di(C1-C4 alkyl)amino group or a saturated 4-8-membered heterocyclic group having a nitrogen atom, still more preferably a dimethylamino group, a methylethylamino group, a diethylamino group, a methylisopropylamino group, a 1-piperidinyl group or a 1-pyrrolidinyl group, and particularly preferably a dimethylamino group.

While the number of the substituent is not particularly limited, it is preferably 1.

The "optionally substituted C1-C6 alkyl group" represented by $R_4$, $R_5$ or $R_6$ is: preferably a C1-C6 alkyl group which may have, as a substituent, a di(C1-C6 alkyl)amino group or a saturated 4-8-membered heterocyclic group containing a nitrogen atom; more preferably a C1-C4 alkyl group which may have, as a substituent, a di(C1-C6 alkyl) amino group or a saturated 4-8-membered heterocyclic group containing a nitrogen atom; more preferably a methyl group, an ethyl group, a n-propyl group, an isopropyl group, a n-butyl group, an isobutyl group, a sec-butyl group, a tert-butyl group, a dimethylaminomethyl group, a methylethylaminomethyl group, a diethylaminomethyl group, a methylisopropylaminomethyl group, a dimethylaminoethyl group, a diethylaminoethyl group, a 1-piperidinylmethyl group or a 1-pyrrolidinylmethyl group; more preferably a methyl group, an ethyl group, a n-propyl group, an isopropyl group, a n-butyl group, an isobutyl group, a sec-butyl group, a tert-butyl group, a dimethylaminomethyl group, a methylethylaminomethyl group, a diethylaminomethyl group, a methylisopropylaminomethyl group, a dimethylaminoethyl group or a diethylaminoethyl group; still more preferably a methyl group, a dimethylaminomethyl group, a methylethylaminomethyl group, a diethylaminomethyl group or a methylisopropylaminomethyl group; and particularly preferably a dimethylaminomethyl group.

$R_4$, $R_5$ and $R_6$ in the pyrazolo[3,4-d]pyrimidine compound represented by General formula (I) is: preferably identically or differently a hydrogen atom or an optionally substituted C1-C6 alkyl group; more preferably a hydrogen atom or a C1-C6 alkyl group which may have, as a substituent, a di(C1-C6 alkyl)amino group or a saturated 4-8-membered heterocyclic group having a nitrogen atom; more preferably a hydrogen atom or a C1-C4 alkyl group which may have, as a substituent, a di(C1-C4 alkyl)amino group or a saturated 4-8-membered heterocyclic group having a nitrogen atom; more preferably a hydrogen atom, a methyl group, an ethyl group, a n-propyl group, an isopropyl group, a n-butyl group, an isobutyl group, a sec-butyl group, a tert-butyl group, a dimethylaminomethyl group, a methylethylaminomethyl group, a diethylaminomethyl group, a methylisopropylaminomethyl group, a dimethylaminoethyl group, a diethylaminoethyl group, a 1-piperidinylmethyl group or a 1-pyrrolidinylmethyl group; more preferably a hydrogen atom, a methyl group, an ethyl group, a n-propyl group, an isopropyl group, a n-butyl group, an isobutyl group, a sec-butyl group, a tert-butyl group, a dimethylaminomethyl group, a methylethylaminomethyl group, a diethylaminomethyl group, a methylisopropylaminomethyl group, a dimethylaminoethyl group or a diethylaminoethyl group; still more preferably a hydrogen atom, a methyl group, a dimethylaminomethyl group, a methylethylaminomethyl group, a diethylaminomethyl group or a methylisopropylaminomethyl group; and particularly preferably a hydrogen atom or a dimethylaminomethyl group.

"—C($R_4$)=C($R_5$)($R_6$)" represented by Y in the pyrazolo [3,4-d]pyrimidine compound represented by General formula (I) is preferably

[Chemical formula 4]

and particularly preferably

[Chemical formula 5]

The pyrazolo[3,4-d]pyrimidine compound represented by General formula (I) is more preferably a compound wherein:

X is a saturated, optionally substituted nitrogen-containing 4-10-membered heterocyclic group;

Y is —C($R_4$)=C($R_5$)($R_6$);

$Z_1$, $Z_2$, $Z_3$ and $Z_4$ are identically or differently a hydrogen atom, a halogen atom, a cyano group, a C2-C6 alkenyl group, an optionally substituted C1-C6 alkoxy group, an optionally substituted C1-C6 alkyl group, an optionally substituted amino group, an optionally substituted C3-C7 cycloalkyl group, a C6-C14 aromatic hydrocarbon group or an unsaturated 4-14-membered heterocyclic group, or $Z_1$ and $Z_2$ or $Z_3$ and $Z_4$ may form, together with carbon atoms that bind thereto, a benzene ring or a saturated or unsaturated 5-7-membered heterocycle;

W is —$CH_2$—, an oxygen atom or —NH—;

n is an integer of 0 to 2;

$R_1$ is an optionally substituted amino group;

$R_2$ and $R_3$ are identically or differently a hydrogen atom, an optionally substituted C1-C6 alkoxy group, an optionally substituted C1-C6 alkyl group or an optionally substituted C6-C14 aromatic hydrocarbon group, or $R_2$ and $R_3$, together with a nitrogen atom that binds thereto, may form a saturated nitrogen-containing 4-8-membered heterocyclic group which may have a hydroxyl group as a substituent; and $R_4$, $R_5$ and $R_6$ are identically or differently a hydrogen atom or an optionally substituted C1-C6 alkyl group, or a salt thereof

The pyrazolo[3,4-d]pyrimidine compound represented by General formula (I) is more preferably a compound wherein:

X is a saturated nitrogen-containing 4-10-membered heterocyclic group which may have a halogen atom, a hydroxyl group, a cyano group, a C1-C6 alkyl group or an amino group as a substituent;

Y is —C(R$_4$)=C(R$_5$)(R$_6$);
Z$_1$, Z$_2$, Z$_3$ and Z$_4$ are identically or differently a hydrogen atom, a halogen atom, a cyano group, a C2-C6 alkenyl group, an optionally substituted C1-C6 alkoxy group, an optionally substituted C1-C6 alkyl group, an optionally substituted amino group, an optionally substituted C3-C7 cycloalkyl group or an unsaturated 4-14-membered heterocyclic group, or Z$_1$ and Z$_2$ or Z$_3$ and Z$_4$ may form, together with carbon atoms that bind thereto, a benzene ring or a saturated or unsaturated 5-7-membered heterocycle;
W is —CH$_2$—, an oxygen atom or —NH—;
n is 0;
R$_1$ is an amino group;
R$_2$ and R$_3$ are identically or differently a hydrogen atom, an optionally substituted C1-C6 alkoxy group, an optionally substituted C1-C6 alkyl group or an optionally substituted C6-C14 aromatic hydrocarbon group, or R$_2$ and R$_3$, together with a nitrogen atom that binds thereto, may form a saturated nitrogen-containing 4-8-membered heterocyclic group which may have a hydroxyl group as a substituent; and
R$_4$, R$_5$ and R$_6$ are identically or differently a hydrogen atom or an optionally substituted C1-C6 alkyl group, or a salt thereof.
The pyrazolo[3,4-d]pyrimidine compound represented by General formula (I) is more preferably a compound wherein:
X is a saturated nitrogen-containing 4-8-membered heterocyclic group which may have a halogen atom or a C1-C6 alkyl group as a substituent;
Y is —C(R$_4$)=C(R$_5$)(R$_6$);
Z$_1$, Z$_2$, Z$_3$ and Z$_4$ are identically or differently a hydrogen atom, a halogen atom, a cyano group, a C2-C6 alkenyl group, a C1-C6 alkoxy group which may be substituted with a halogen atom, a C1-C6 alkyl group, an amino group which may be substituted with a C1-C6 alkyl group, a C3-C7 cycloalkyl group or an unsaturated 4-6-membered heteromonocyclic group having one oxygen atom, or Z$_1$ and Z$_2$ or Z$_3$ and Z$_4$ may form, together with carbon atoms that bind thereto, a benzene ring or a saturated or unsaturated 5-7-membered heterocycle;
W is —CH$_2$—, an oxygen atom or —NH—;
n is 0;
R$_1$ is an amino group;
R$_2$ and R$_3$ are identically or differently a hydrogen atom, a C1-C6 alkoxy group, a C1-C6 alkyl group or a C6-C14 aromatic hydrocarbon group, or R$_2$ and R$_3$, together with a nitrogen atom that binds thereto, may form a saturated nitrogen-containing 4-8-membered heterocyclic group which may be substituted with a hydroxyl group; and
R$_4$, R$_5$ and R$_6$ are identically or differently a hydrogen atom or a C1-C6 alkyl group which may be substituted with a di(C1-C6 alkyl)amino group,
or a salt thereof.
The pyrazolo[3,4-d]pyrimidine compound represented by General formula (I) is more preferably a compound wherein:
X is a pyrrolidinyl group which may have a C1-C6 alkyl group as a substituent or a piperidinyl group which may have a halogen atom as a substituent;
Y is —C(R$_4$)=C(R$_5$)(R$_6$);
Z$_1$, Z$_2$, Z$_3$ and Z$_4$ are identically or differently a hydrogen atom, a halogen atom, a cyano group, a C2-C6 alkenyl group, a C1-C6 alkoxy group which may be substituted with a halogen atom, a C1-C6 alkyl group, an amino group which may be substituted with a C1-C6 alkyl group, a C3-C7 cycloalkyl group or an unsaturated 4-6-membered heteromonocyclic group having one oxygen atom, or Z$_1$ and Z$_2$ or Z$_3$ and Z$_4$ may form, together with carbon atoms that bind thereto, a benzene ring or a saturated or unsaturated 5-7-membered heterocycle;
W is —CH$_2$—, an oxygen atom or —NH—;
n is 0;
R$_1$ is an amino group;
R$_2$ and R$_3$ are identically or differently a hydrogen atom, a C1-C6 alkoxy group, a C1-C6 alkyl group or a C6-C14 aromatic hydrocarbon group, or R$_2$ and R$_3$ may form, together with a nitrogen atom that binds thereto, a saturated nitrogen-containing 4-8-membered heterocyclic group which may be substituted with a hydroxyl group; and
R$_4$, R$_5$ and R$_6$ are identically or differently a hydrogen atom or a dimethylaminomethyl group,
or a salt thereof.
The pyrazolo[3,4-d]pyrimidine compound represented by General formula (I) is more preferably a compound wherein:
X is a pyrrolidinyl group, a methylpyrrolidinyl group, a piperidinyl group or a fluoropiperidinyl group;
Y is:

[Chemical formula 6]

Z$_1$, Z$_2$, Z$_3$ and Z$_4$ are identically or differently a hydrogen atom, a fluorine atom, a chlorine atom, a bromine atom, a cyano group, a vinyl group, a methoxy group which may have a fluorine atom as a substituent, a methyl group, an ethyl group, a dimethylamino group, a cyclopropyl group or a furyl group, or Z$_1$ and Z$_2$ or Z$_3$ and Z$_4$ may form, together with carbon atoms that bind thereto, a benzene ring, a pyridine ring or a dioxolane ring;
W is —CH$_2$—, an oxygen atom or —NH—;
n is 0;
R$_1$ is an amino group; and
R$_2$ and R$_3$ are identically or differently a hydrogen atom, a methoxy group, a methyl group or a phenyl group, or R$_2$ and R$_3$ may form, together with a nitrogen atom that binds thereto, an azetidinyl group, a pyrrolidinyl group or a piperidinyl group, which may have a hydroxyl group as a substituent, or a salt thereof.
The pyrazolo[3,4-d]pyrimidine compound represented by General formula (I) is more preferably a compound wherein:
X is a pyrrolidinyl group, a methylpyrrolidinyl group, a piperidinyl group or a fluoropiperidinyl group;
Y is:

[Chemical formula 7]

Z$_1$, Z$_2$, Z$_3$ and Z$_4$ are identically or differently a hydrogen atom, a fluorine atom, a chlorine atom, a bromine atom, a cyano group, a vinyl group, a methoxy group, a fluoromethoxy group, a difluoromethoxy group, a methyl group, an ethyl group, a dimethylamino group, a cyclopropyl group or a furyl group, or $Z_1$ and $Z_2$ or $Z_3$ and $Z_4$ may form, together with carbon atoms that bind thereto, a benzene ring, a pyridine ring or a dioxolane ring;

W is —$CH_2$—, an oxygen atom or —NH—;

n is 0;

$R_1$ is an amino group; and

$R_2$ and $R_3$ are identically or differently a methoxy group, a methyl group or a phenyl group, or $R_2$ and $R_3$ may form, together with a nitrogen atom that binds thereto, a hydroxyazetidinyl group, a pyrrolidinyl group or a piperidinyl group, or a salt thereof.

The pyrazolo[3,4-d]pyrimidine compound represented by General formula (I) is more preferably a compound wherein:

X is a pyrrolidinyl group, a methylpyrrolidinyl group, a piperidinyl group or a fluoropiperidinyl group;

Y is:

[Chemical formula 8]

$Z_1$, $Z_2$, $Z_3$ and $Z_4$ are identically or differently a hydrogen atom, a fluorine atom, a chlorine atom, a bromine atom, a cyano group, a vinyl group, a methoxy group, a fluoromethoxy group, a difluoromethoxy group, a methyl group, an ethyl group, a dimethylamino group, a cyclopropyl group or a furyl group, or $Z_1$ and $Z_2$ or $Z_3$ and $Z_4$ may form, together with carbon atoms that bind thereto, a benzene ring, a pyridine ring or a dioxolane ring;

W is —$CH_2$— or an oxygen atom;

n is 0;

$R_1$ is an amino group; and

$R_2$ and $R_3$ are identically or differently a methoxy group, a methyl group or a phenyl group, or $R_2$ and $R_3$ may form, together with a nitrogen atom that binds thereto, a hydroxyazetidinyl group, a pyrrolidinyl group or a piperidinyl group, or a salt thereof.

The pyrazolo[3,4-d]pyrimidine compound represented by General formula (I) is more preferably a compound wherein:

X is a pyrrolidinyl group, a methylpyrrolidinyl group, a piperidinyl group or a fluoropiperidinyl group;

Y is:

[Chemical formula 9]

$Z_1$, $Z_2$, $Z_3$ and $Z_4$ are identically or differently a hydrogen atom, a fluorine atom, a chlorine atom, a bromine atom, a cyano group, a vinyl group, a methoxy group, a fluoromethoxy group, a difluoromethoxy group, a methyl group, an ethyl group, a dimethylamino group, a cyclopropyl group or a furyl group, or $Z_1$ and $Z_2$ or $Z_3$ and $Z_4$ may form, together with carbon atoms that bind thereto, a benzene ring, a pyridine ring or a dioxolane ring;

W is —$CH_2$— or an oxygen atom;

n is 0;

$R_1$ is an amino group; and $R_2$ and $R_3$ are methyl groups, or a salt thereof.

The pyrazolo[3,4-d]pyrimidine compound represented by General formula (I) is more preferably a compound wherein:

X is a piperidinyl group or a fluoropiperidinyl group;

Y is:

[Chemical formula 10]

$Z_1$, $Z_2$, $Z_3$ and $Z_4$ are identically or differently a hydrogen atom, a fluorine atom, a chlorine atom, a bromine atom, a cyano group, a vinyl group, a methoxy group, a fluoromethoxy group, a difluoromethoxy group, a methyl group, an ethyl group, a dimethylamino group, a cyclopropyl group or a furyl group, or $Z_1$ and $Z_2$ or $Z_3$ and $Z_4$ may form, together with carbon atoms that bind thereto, a benzene ring, a pyridine ring or a dioxolane ring;

W is —$CH_2$— or an oxygen atom;

n is 0;

$R_1$ is an amino group; and $R_2$ and $R_3$ are methyl groups, or a salt thereof The pyrazolo[3,4-d]pyrimidine compound represented by General formula (I) is more preferably a compound wherein:

X is a piperidinyl group;

Y is:

[Chemical formula 11]

$Z_1$, $Z_2$, $Z_3$ and $Z_4$ are identically or differently a hydrogen atom, a fluorine atom, a chlorine atom, a bromine atom, a methoxy group, a fluoromethoxy group, a difluoromethoxy group or a methyl group, or $Z_1$ and $Z_2$ or $Z_3$ and $Z_4$ may form, together with carbon atoms that bind thereto, a benzene ring;

W is —$CH_2$—;

n is 0;

$R_1$ is an amino group; and $R_2$ and $R_3$ are methyl groups, or a salt thereof.

Example of specific pyrazolo[3,4-d]pyrimidine compounds that can be used in the present invention include, but not limited to, the exemplary compounds 1 to 79 described in International Patent Application Publication WO2017/038838.

Examples of more preferable pyrazolo[3,4-d]pyrimidine compounds include the followings:

(1) (R)-1-(1-acryloylpiperidine-3-yl)-4-amino-N-(5-bromo-4-(2-(dimethylamino)-2-oxoethyl)-2-methylphenyl)-1H-pyrazolo[3,4-d]pyrimidine-3-carboxamide, (2) (R)-1-(1-acryloylpiperidine-3-yl)-4-amino-N-(2-chloro-4-(2-(dimethylamino)-2-oxoethyl)-5-methylphenyl)-1H-pyrazolo[3,4-d]pyrimidine-3-carboxamide, (3) (R)-1-(1-acryloylpiperidine-3-yl)-4-amino-N-(2-chloro-4-(2-(dimethylamino)-2-oxoethyl)-3-methylphenyl)-1H-pyrazolo[3,4-d]pyrimidine-3-carboxamide, (4) (R)-1-(1-acryloylpiperidine-3-yl)-4-amino-N-(4-(2-(dimethylamino)-2-oxoethyl)-2-methylphenyl)-1H-pyrazolo[3,4-d]pyrimidine-3-carboxamide, (5) (R)-1-(1-acryloylpiperidine-3-yl)-4-amino-N-(4-(2-(dimethylamino)-2-oxoethyl)naphthalene-1-yl)-1H-pyrazolo[3,4-d]pyrimidine-3-carboxamide,
(6) (R)-1-(1-acryloylpiperidine-3-yl)-4-amino-N-(2-chloro-4-(2-(dimethylamino)-2-oxoethyl)phenyl)-1H-pyrazolo[3,4-d]pyrimidine-3-carboxamide,
(7) (R)-1-(1-acryloylpiperidine-3-yl)-4-amino-N-(4-(2-(dimethylamino)-2-oxoethyl)-2-methoxyphenyl)-1H-pyrazolo[3,4-d]pyrimidine-3-carboxamide, acryloylpiperidine-3-yl)-4-amino-N-(2,5-dichloro-4-(2-(dimethylamino)-2-oxoethyl)phenyl)-1H-pyrazolo[3,4-d]pyrimidine-3-carboxamide.

An example of a still more preferable pyrazolo[3,4-d]pyrimidine compound includes (R)-1-(1-acryloylpiperidine-3-yl)-4-amino-N-(4-(2-(dimethylamino)-2-oxoethyl)-2,3-dimethylphenyl)-1H-pyrazolo[3,4-d]pyrimidine-3-carboxamide (hereinafter, referred to as "Compound 1") shown in Table 1.

TABLE 1

| Structural formula | NMR | mass |
|---|---|---|
|  | 1H NMR (400 MHZ, DMSO-6) Shift 1,52-1.69 (m, 1H), 1.92-2.03 (m, 1H), 2.06-2.41 (m, 2H), 2.10 (s, 3H), 2.13 (s, 3H), 2.85 (s, 3H), 2.99-3.24 (m, 1H), 3.05 (s, 3H), 3.29-3.85 (m, 1H), 3.33 (s, 2H), 3.99-4.58 (m, 2H), 4.67-4.81 (m, 1H), 5.58-5.73 (m, 1H), 6.05-6.15 (m, 1H), 6.71-6.96 (m, 1H), 6.95 (d, J = 8.0 Hz, 1H), 7.10-7.15 (m, 1H), 8.09 (br s, 1H), 8.26 (s, 1H), 8.60 (br s, 1H), 10.11-10.24 (m, 1H). | 505.3 |

(8) (R)-1-(1-acryloylpiperidine-3-yl)-4-amino-N-(3-chloro-4-(2-(dimethylamino)-2-oxoethyl)phenyl)-1H-pyrazolo[3,4-d]pyrimidine-3-carboxamide,
(9) (R)-1-(1-acryloylpiperidine-3-yl)-4-amino-N-(5-chloro-4-(2-(dimethylamino)-2-oxoethyl)-2-methoxyphenyl)-1H-pyrazolo[3,4-d]pyrimidine-3-carboxamide,
(10) (R)-1-(1-acryloylpiperidine-3-yl)-4-amino-N-(4-(2-(dimethylamino)-2-oxoethyl)-5-fluoro-2-methylphenyl)-1H-pyrazolo[3,4-d]pyrimidine-3-carboxamide,
(11) (R)-1-(1-acryloylpiperidine-3-yl)-4-amino-N-(3-chloro-4-(2-(dimethylamino)-2-oxoethyl)-2-methoxyphenyl)-1H-pyrazolo[3,4-d]pyrimidine-3-carboxamide,
(12) (R)-1-(1-acryloylpiperidine-3-yl)-4-amino-N-(4-(2-(dimethylamino)-2-oxoethyl)-3-fluoro-2-methylphenyl)-1H-pyrazolo[3,4-d]pyrimidine-3-carboxamide,
(13) (R)-1-(1-acryloylpiperidine-3-yl)-4-amino-N-(4-(2-(dimethylamino)-2-oxoethyl)-2,3-dimethylphenyl)-1H-pyrazolo[3,4-d]pyrimidine-3-carboxamide,
(14) (R)-1-(1-acryloylpiperidine-3-yl)-4-amino-N-(4-(2-(dimethylamino)-2-oxoethyl)-3-fluoro-2-methoxyphenyl)-1H-pyrazolo[3,4-d]pyrimidine-3-carboxamide,
(15) (R)-1-(1-acryloylpiperidine-3-yl)-4-amino-N-(2-(difluoromethoxy)-4-(2-(dimethylamino)-2-oxoethyl)phenyl)-1H-pyrazolo[3,4-d]pyrimidine-3-carboxamide,
(16) (R)-1-(1-acryloylpiperidine-3-yl)-4-amino-N-(4-(2-(dimethylamino)-2-oxoethyl)-2-(fluoromethoxy)phenyl)-1H-pyrazolo[3,4-d]pyrimidine-3-carboxamide,
(17) (R)-1-(1-acryloylpiperidine-3-yl)-4-amino-N-(2-bromo-4-(2-(dimethylamino)-2-oxoethyl)phenyl)-1H-pyrazolo[3,4-d]pyrimidine-3-carboxamide, (18) (R)-1-(1-acryloylpiperidine-3-yl)-4-amino-N-(2-chloro-4-(2-(dimethylamino)-2-oxoethyl)-5-fluorophenyl)-1H-pyrazolo[3,4-d]pyrimidine-3-carboxamide, (19) (R)-1-(1-acryloylpiperidine-3-yl)-4-amino-N-(5-chloro-4-(2-(dimethylamino)-2-oxoethyl)-2-methylphenyl)-1H-pyrazolo[3,4-d]pyrimidine-3-carboxamide, (20) (R)-1-(1-

The salt of the pyrazolo[3,4-d]pyrimidine compound represented by General formula (I) is not particularly limited as long as it is a pharmaceutically acceptable salt and refers to one that is commonly used in the field of organic chemistry. Examples of such salt include salts such as a base-added salt of a carboxyl group when the compound has the carboxyl group, and an acid-added salt of an amino group or a basic heterocyclic group when the compound has the amino group or the basic heterocyclic group.

Examples of said base-added salt include: alkali metal salts such as a sodium salt and a potassium salt; alkaline earth metal salts such as a calcium salt and a magnesium salt; ammonium salts; and organic amine salts such as a trimethylamine salt, a triethylamine salt, a dicyclohexylamine salt, an ethanolamine salt, a diethanolamine salt, a triethanolamine salt, a procaine salt and a N,N'-dibenzylethylenediamine salt. Examples of said acid-added salt include: inorganic acid salts such as a hydrochloride, a sulfate, a nitrate, a phosphate and a perchlorate; organic acid salts such as an acetate, a formate, a maleate, a fumarate, a tartrate, a citrate, an ascorbate and a trifluoroacetate; and sulfonates such as a methanesulfonate, an isethionate, a benzenesulfonate and a p-toluenesulfonate.

The pyrazolo[3,4-d]pyrimidine compound represented by General formula (I) or a salt thereof used in the present invention may be synthesized, for example, according to the process described in the pamphlet of International Patent Application Publication WO2017/038838. The manufacturing process or the synthesis example of the pyrazolo[3,4-d]pyrimidine compound represented by General formula (I) or a salt thereof is not limited to the process described in said pamphlet.

According to the present invention, the term "other antitumor agents" refers to clinically employed antitumor agents other than the pyrazolo[3,4-d]pyrimidine compound represented by General formula (I) used in the present invention.

While "other antitumor agents" are not particularly limited as long as they are antitumor agents as described above, they are preferably doxorubicin, paclitaxel, bevacizumab, carboplatin or an anti-HER2 antibody (trastuzumab, pertuzumab, trastuzumab emtansine, etc.), more preferably an anti-HER2 antibody such as trastuzumab, pertuzumab, trastuzumab emtansine, DS-8201 (trastuzumab deruxtecan), SYD985 (trastuzumab duocarmazine), XMT-1522 or MEDI4276, more preferably trastuzumab, pertuzumab, trastuzumab emtansine, DS-8201 (trastuzumab deruxtecan) or SYD985 (trastuzumab duocarmazine), still more preferably trastuzumab, trastuzumab emtansine or pertuzumab, and yet still more preferably trastuzumab or trastuzumab emtansine. "Other antitumor agents" may be, for example, antitumor agents employed in standard treatments.

According to the present invention, the "resistance or intractability to other antitumor agents" may refer to resistance or intractability that is acquired via a treatment with other antitumor agent, or intrinsic resistance or intractability irrelevant to treatments with other antitumor agents.

The "resistance or intractability that is acquired via a treatment with other antitumor agent" is: preferably resistance or intractability that is acquired via a treatment with a HER2 inhibitor; more preferably resistance or intractability that is acquired via a treatment with an anti-HER2 antibody; more preferably resistance or intractability that is acquired via a treatment with trastuzumab, pertuzumab, trastuzumab emtansine, DS-8201 (trastuzumab deruxtecan) or SYD985 (trastuzumab duocarmazine); still more preferably resistance or intractability that is acquired via a treatment with trastuzumab, trastuzumab emtansine or pertuzumab; and yet still more preferably resistance or intractability that is acquired via a treatment with trastuzumab or trastuzumab emtansine.

The "intrinsic resistance or intractability irrelevant to treatments with other antitumor agents" is: preferably intrinsic resistance or intractability to a HER2 inhibitor irrelevant to a treatment with a HER2 inhibitor; more preferably intrinsic resistance or intractability to an anti-HER2 antibody irrelevant to a treatment with the anti-HER2 antibody; more preferably intrinsic resistance or intractability to trastuzumab, pertuzumab, trastuzumab emtansine, DS-8201 (trastuzumab deruxtecan) or SYD985 (trastuzumab duocarmazine) irrelevant to a treatment with trastuzumab, pertuzumab, trastuzumab emtansine, DS-8201 (trastuzumab deruxtecan) or SYD985 (trastuzumab duocarmazine); still more preferably intrinsic resistance or intractability to trastuzumab, trastuzumab emtansine or pertuzumab irrelevant to a treatment with trastuzumab, trastuzumab emtansine or pertuzumab; and yet still more preferably intrinsic resistance or intractability to trastuzumab or trastuzumab emtansine irrelevant to a treatment with trastuzumab or trastuzumab emtansine.

According to the present invention, the "resistance or intractability to other antitumor agents" comprises resistance to other antitumor agents, intolerance to other antitumor agents, exacerbation following chemotherapy with other antitumor agents, and recurrence following chemotherapy with other antitumor agents.

According to the present invention, a "HER2 inhibitor" refers to a drug that targets HER2 except the pyrazolo[3,4-d]pyrimidine compound represented by General formula (I) used in the present invention, and preferably is a HER2 inhibitor used in a standard treatment. Herein, the HER2 inhibitor may also have a function of targeting other target molecule as long as it has a function of targeting HER2.

Examples of the HER2 inhibitor include trastuzumab, trastuzumab emtansine, pertuzumab and lapatinib. The HER2 inhibitor is preferably an anti-HER2 antibody, more preferably trastuzumab, trastuzumab emtansine or pertuzumab, more preferably trastuzumab, pertuzumab, trastuzumab emtansine, DS-8201 (trastuzumab deruxtecan) or SYD985 (trastuzumab duocannazine), still more preferably trastuzumab or trastuzumab emtansine, and yet still more preferably trastuzumab.

Examples of preferable embodiments of the anti-HER2 antibody include trastuzumab and antibody-drug conjugates which have trastuzumab as the antibody (for example, trastuzumab emtansine, DS-8201 and SYD985).

Herein, "HER2" comprises human or non-human mammal HER2, preferably human HER2. In addition, the term "HER2" comprises its isoforms.

Cancer targeted by the present invention is preferably cancer on which the pyrazolo[3,4-d]pyrimidine compound represented by General formula (I) or a salt thereof can exert an anti-tumor effect, and more preferably HER2-associated malignant tumor. Herein, a "HER2-associated malignant tumor" comprises malignant tumors whose incidence can be decreased and whose symptoms can be ameliorated, alleviated and/or cured by deleting, suppressing and/or inhibiting the function of HER2.

Such a malignant tumor is preferably a malignant tumor which is associated with overexpression of HER2, amplification of HER2 gene or mutation in HER2. While the above-described "malignant tumor" to be targeted is not particularly limited, examples thereof include head and neck cancer, esophageal cancer, stomach cancer, colon cancer, rectal cancer, liver cancer, gallbladder and bile duct cancer, biliary tract cancer, pancreatic cancer, lung cancer, breast cancer, ovarian cancer, cervical cancer, endometrial cancer, renal cancer, bladder cancer, prostate cancer, testicular tumor, bone and soft tissue sarcomas, blood cancer, multiple myeloma, skin cancer, brain tumor and mesothelioma. The above-described "malignant tumor" is preferably breast cancer, stomach cancer, esophageal cancer, ovarian cancer, lung cancer, gallbladder and bile duct cancer, biliary tract cancer, bladder cancer or colon cancer, more preferably breast cancer, stomach cancer, esophageal cancer, biliary tract cancer, ovarian cancer or lung cancer, and more preferably breast cancer or stomach cancer.

According to the present invention, a "HER2-positive tumor which is resistant or intractable to other antitumor agents" is preferably the above-described malignant tumor that is resistant or intractable to other antitumor agents, more preferably HER2-positive breast cancer resistant or intractable to other antitumor agents or HER2-positive stomach cancer resistant or intractable to other antitumor agents. In one embodiment of the present invention, a "HER2-positive tumor which is resistant or intractable to other antitumor agents" may be HER2-positive breast cancer resistant or intractable to other antitumor agents. In another embodiment of the present invention, a "HER2-positive tumor which is resistant or intractable to other antitumor agents" may be HER2-positive stomach cancer resistant or intractable to other antitumor agents. Furthermore, according to the present invention, a "HER2-positive tumor which is resistant or intractable to other antitumor agents" may be, for example, but not limited to, a trastuzumab-resistant tumor, a trastuzumab emtansine-resistant tumor or a pertuzumab-resistant tumor.

When the pyrazolo[3,4-d]pyrimidine compound represented by General formula (I) or a salt thereof is used as a medicine, various dosage forms can be employed according to the therapeutic purpose by adding a pharmacological carrier as necessary, where such form may be, for example, any of an oral agent, an injectable agent, a suppository, an ointment, a patch and the like. These dosage forms can be manufactured according to a common formulation process commonly known to those skilled in the art.

Any organic or inorganic carrier substance common as a formulation material can be used as the pharmacological carrier, which can be added as an excipient, a binder, a disintegrant, a lubricant, a coating agent or the like in a solid formulation or as a solvent, a solubilizing adjuvant, a suspending agent, an isotonicity agent, a pH regulator/buffer, an analgesic or the like in a liquid formulation. In addition, formulation additives such as an antiseptic, an antioxidant, a colorant, a flavoring agent, a stabilizer and the like can also be used, as necessary.

Examples of the excipient include lactose, white sugar, D-mannitol, starch, microcrystalline cellulose and calcium silicate.

Examples of the binder include hydroxypropyl cellulose, methyl cellulose, polyvinylpyrrolidone, powdered starch syrup and hypromellose.

Examples of the disintegrant include sodium starch glycolate, carmellose calcium, croscarmellose sodium, crospovidone, low-substituted hydroxypropyl cellulose and partially pregelatinized starch.

Examples of the lubricant include talc, magnesium stearate, sucrose fatty acid esters, stearic acid and sodium stearyl fumarate.

Examples of the coating agent include ethyl cellulose, an aminoalkyl methacrylate copolymer RS, hypromellose and white sugar.

Examples of the solvent include water, propylene glycol and physiological saline.

Examples of the solubilizing adjuvant include polyethylene glycol, ethanol, α-cyclodextrin, Macrogol 400 and polysorbate 80.

Examples of the suspending agent include carrageenan, microcrystalline cellulose/carmellose sodium, and polyoxyethylene hydrogenated castor oil.

Examples of the isotonicity agent include sodium chloride, glycerol and potassium chloride.

Examples of the pH regulator/buffer include sodium citrate, hydrochloric acid, lactic acid, phosphoric acid and sodium dihydrogen phosphate.

Examples of the analgesic include procaine hydrochloride and lidocain.

Examples of the antiseptic include ethylpara-hydroxybenzoate, cresol and benzalkonium chloride.

Examples of the antioxidant include sodium sulfite, ascorbic acid and naturally occurring vitamin E.

Examples of the colorant include titanium oxide, iron sesquioxide, Food Blue No. 1 and copper chlorophyll.

Examples of the flavoring agent include aspartame, saccharin, sucralose, l-menthol and mint flavor.

Examples of the stabilizer include sodium pyrosulfite, sodium edetate, erythorbic acid, magnesium oxide and dibutyl hydroxytoluene.

If a solid oral formulation is to be prepared, an excipient, a binder, a disintegrant, a lubricant, a colorant, a flavoring agent or the like can be used to manufacture a tablet, a coated tablet, granules, powder, a capsule or the like according to a common method.

If an injectable agent is to be prepared, a pH regulator, a buffer, a stabilizer, an isotonicity agent, a local anesthetic or the like can be used to manufacture an injectable agent for subcutaneous, intramuscular or intravenous administration or the like according to a common method.

While the amount of the pyrazolo[3,4-d]pyrimidine compound or a salt thereof that should be added to each of the above-described unit dosage form varies depending on the symptoms of the patient who is given this dosage form or depending on the form of this dosage, in general, it is preferably 0.05-1,000 mg per unit dosage form in a case of an oral agent, 0.01-500 mg in a case of an injectable agent, and 1-1,000 mg in a case of a suppository.

The daily dose of the pyrazolo[3,4-d]pyrimidine compound or a salt thereof in the above-described dosage form varies depending on the symptom, weight, age, sex and the like of the patient and thus cannot simply be determined but usually the daily dose in terms of the pyrazolo[3,4-d]pyrimidine compound may be 0.05-5,000 mg and preferably 0.1-1,000 mg for an adult (weight 50 kg), which is preferably administered once or a few times a day.

The present invention also relates to a formulation kit which includes a pyrazolo[3,4-d]pyrimidine compound or a salt thereof used in the present invention, and instructions for use specifying that the pyrazolo[3,4-d]pyrimidine compound or a salt thereof used in the present invention is administered to a HER2-positive tumor which is resistant or intractable to other antitumor agents. Herein, while "instructions for use" may be of any kind as long as it describes the above-mentioned dose with or without a legal restriction, it preferably recommends the above-mentioned dose. Specific examples of the instructions for use include an attached document, a pamphlet or the like. Moreover, a formulation kit including instructions for use may mean that the instructions for use is printed on or attached to the package of the formulation kit, or instructions for use is enclosed together with the antitumor agent in the package of the formulation kit.

EXAMPLES

Hereinafter, the present invention will be described more specifically by means of examples, although the present invention should not be limited in any way to these examples.

Test Example 1: Test for Antitumor Evaluation in Model with Tumor Recurrence Following Administration of Trastuzumab Emtansine Human stomach cancer cell line, NCI-N87, was obtained from American Type Culture Collection (ATCC). The cell line was cultured in a RPMI-1640 medium (containing 4.5 g/L glucose, 10 mM HEPES and 1 mM sodium pyruvate) (Wako Pure Chemical Corporation) containing 10% fetal bovine serum (FBS) at 37° C. in a 5% $CO_2$ incubator.

The NCI-N87 cells were resuspended in PBS to a concentration of $10^8$ cells/mL. A 1-mL tuberculin syringe with a 25G needle was used to subcutaneously transplant $8 \times 10^6$ cells/0.1 mL each of the cell suspension into the right chests of 6-week-old nude mice (BALB/cAJcl-nu/nu, CLEA Japan, Inc.).

The tumor diameter was measured with a digital caliper by holding the long diameter and the short diameter of the tumor between the measuring surfaces of the digital caliper for each mouse. Measurements took place at a frequency of once in 2-5 days including the day of group sorting and the day of judgement. The tumor volume (TV) was calculated based on these long and short diameters. The relative tumor volume (RTV) and the rate of change in the relative tumor volume (T/C) were calculated from the calculated tumor volume. TV, RTV and T/C were calculated according to the following equations.

Tumor volume TV(mm³)=(Long diameter, mm)× (Short diameter, mm)×(Short diameter, mm)/2

Relative tumor volume RTV=(TV on day of measurement)/(TV on day of dividing into groups)

Rate of change in relative tumor volume T/C (%)= (Mean RTV of treated group)/(Mean RTV of control group)×100

Furthermore, an electronic balance for animals was used to measure the weights. The rate of change in the weight on Day n (BWCn) was calculated from the weight on Day n (BWn) according to the following equation.

Rate of change in weight BWCn (%)=(BWn−BW0)/BW0×100

Step 1: Preparation of Model with Tumor Recurrence Following Administration of Trastuzumab Emtansine Nude mice with TV of 100-300 mm³ were selected, and 6 animals were assigned to the control group while 36 animals were assigned to the trastuzumab emtansine-administered group by equal distribution (MiSTAT (ver.2.0)), such that the mean TV of each group was equal (Day 0). Trastuzumab emtansine (Kadcyla, Roche) was prepared to 1 mg/mL with Otsuka normal saline, and the resultant was administered into the tail vein of each animal once a day on Days 1, 22, 43 and 64. The tumor diameters and weights were measured with time to calculate TV and BWC.

TABLE 2

| Group | Dose (mg/kg/day) | Schedule (day) | Route | n |
|---|---|---|---|---|
| Control | — | Non treatment | — | 6 |
| Trastuzumab emtansine | 10 | 1, 22, 43, 64 | i.v. | 36 |

Figure 1:
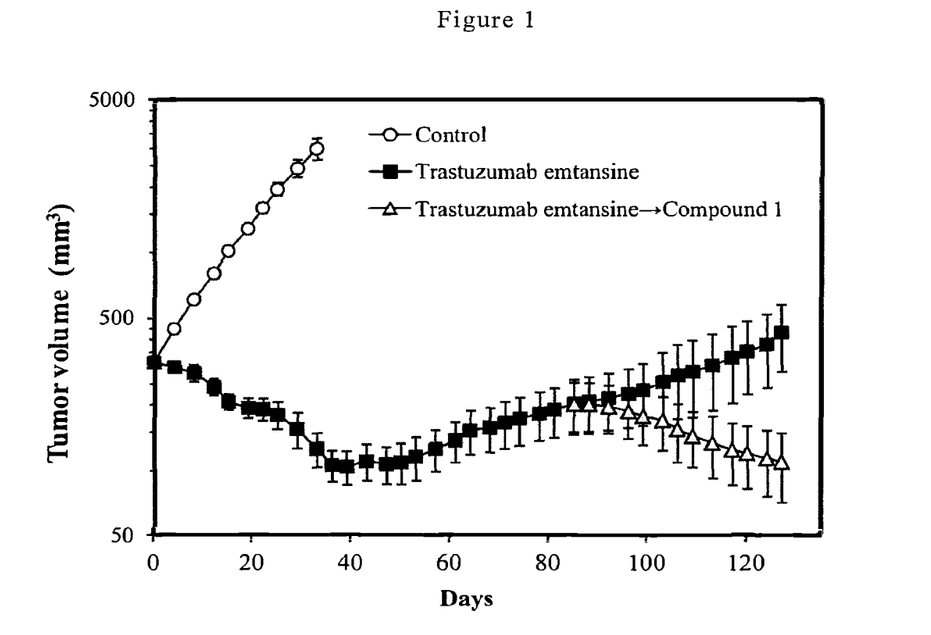
FIG. 1 shows an anti-tumor effect of Compound 1 on models with tumor recurrence after administration of trastuzumab emtansine.

As shown in FIG. 1, tumor shrinkage was confirmed for once by administration of trastuzumab emtansine but tumor recurrence was confirmed on Day 85.

Step 2: Anti-Tumor Effect of Compound 1 on Model with Tumor Recurrence

Eighteen nude mice confirmed with tumor recurrence in Step 1 were selected, and 9 animals were assigned to each group by equal distribution (MiSTAT (ver.2.0)) as follows such that the mean TV of each group was uniform (Day 1, i.e., Day 85 as counted from Step 1). Compound 1 was prepared to 6 mg/mL with a 0.1N HCl solution, and the resultant was orally administered once a day on Days 1-42 consecutively. Trastuzumab emtansine (Kadcyla, Roche) was prepared to 1 mg/mL with Otsuka normal saline, and the resultant was administered into the tail vein of each animal once a day on Days 1 and 22. The tumor diameters and weights were measured with time to calculate TV and BWC.

TABLE 3

| Group | Dose (mg/kg/day) | Schedule (day) | Route | n |
|---|---|---|---|---|
| Trastuzumab emtansine | 10 | 1, 22 [85, 106] | i.v. | 9 |
| Compound 1 | 60 | 1-42 [85-126] | p.o. | 9 |

[]: The Days as counted from Step 1

The results are shown in Table 4 below and in FIG. 1.

TABLE 4

| Group | TV (mm³) on Day43 Mean ± SD | p value [a] vs. Trastuzumab emtansine | T/C (%) [b] | BWC(%) on Day43 [c] Mean |
|---|---|---|---|---|
| Trastuzumab emtansine | 421.92 ± 143.78 | — | — | 21.89 |
| Compound 1 | 107.29 ± 37.76 | 0.0001 | 25.4 | 23.65 |

[a]: p-value was calculated by the Aspin-Welch t-test.
[b]: Treated/Control (T/C) an Day 43 was calculated according to the following formula: T/C (%) = (mean TV of the Compound I group)/(mean TV of the Trastuzumab emtansine group) × 100
[c]: Body weight change (BWC) on Day43 was calculated as the ratio of BW on Day43 to that on Day0 of Step 1 according to the following formula: BWC = (BW on Day43 − BW on Day0 of Step1)/BW on Day0 of Step1 × 100
SD: standard deviation The results from analysis of TV of each group by Aspin-Welch's t-test showed that TV of the Compound-1-administered group was significantly lower than that of the trastuzumab emtansine-administered group on the day of judgement (Day 43). Moreover, no significant decrease in the average rate of change in the weight of the Compound-1-administered group was observed as compared to that of the trastuzumab emtansine-administered group.

Test Example 2: Examination of Anti-Tumor Effect Using Cancer Patient-Derived Cells Champions Tumor Graft models CTG-1171 (Champions Oncology, Inc.) having the profiles shown in Tables 5-8 were transplanted into Stock mice (Athymic Nude-Foxn1$^{nu}$, Envigo). Once the tumor volume of the transplanted tumor reached 1,000-1,500 mm³, the tumor was taken out and a fragment thereof of about 65 mm³ was subcutaneously transplanted into the left side of 7-week-old nude mice (Athymic Nude-Foxn1$^{nu}$, Envigo). Tumor diameters were measured twice a week with a digital caliper. TV was calculated according to the following equation.

TV (mm³)=Width (mm)²×Length (mm)×0.52

Ten individuals whose tumor volumes reached 150-300 mm³ were assigned to each group (Day 0).

Compound 1 was prepared to have a predetermined concentration with a 0.1N HCl solution, and the resultant was orally administered once a day on Days 0-27 consecutively. Tumor diameters were measured twice a week with a digital caliper. The rate of change in the weight of the mouse was calculated in the same manner as Test example 1 above. Mice observed with weight loss by 10% or more as compared to Day 0 were given DietGel (registered trademark).

TABLE 5

Patient and tumor profile

| Sex | Female |
|---|---|
| Cancer type | Breast cancer (primary) |
| Estrogen receptor | – |
| Progesterone receptor | – |
| HER2 | + |

TABLE 6

Treatment history before acquiring tumor tissue

| Treatment history | Period (month) | Result |
|---|---|---|
| Carboplatin<br>Docetaxel<br>Trastuzumab | 4 | Responded |
| Vinorelbine<br>Trastuzumab<br>5-Fluorouracil | N/A | Mixed response |
| Liposomal doxorubicin<br>Paclitaxel<br>Bevacizumab | N/A | No response |
| Carboplatin<br>Trastuzumab<br>Pertuzumab | N/A | No response |
| Trastuzumab emtansine | N/A | No response |

N/A: Not applicable

TABLE 7

Treatment history after acquiring tumor tissue

| Treatment history | Period (Month) | Result |
|---|---|---|
| Capecitabine<br>Lapatinib<br>Trastuzumab | N/A | No response |
| Eribulin | N/A | No response |
| Afatinib | Not available | Not available |
| Trastuzumab emtansine | N/A | No response |

N/A: Not applicable

TABLE 8

PDX using other antitumor agent

| Other antitumor agent | Dose (mg/kg/day) | Schedule | Route | TGI (%) |
|---|---|---|---|---|
| Capecitabine | 5 | Once a day for 21 days | p.o | 96 |
| Lapatinib | 1 | Once a day for 21 days | p.o | |
| Nab-paclitaxel | 0.5 | Once a week for 3 weeks | i.v. | 85 |
| Temsirolimus | 0.5 | Once a week for 5 weeks | i.p. | 59 |
| Trastuzumab | 15 | Once a week for 8 weeks | i.v. | 26 |
| Afatinib | | | | 123 |
| Gemcitabine<br>Nab-paclitaxel | | | | 28 |

TGI of trastuzumab shown in Table 8 is weak, and thus cells derived from the corresponding patients are judged to have tolerance/resistance to trastuzumab.

TABLE 9

| Group | Dose (mg/kg/day) | Schedule (day) | Route | n |
|---|---|---|---|---|
| Control | — | 0-27 | p.o. | 10 |
| Compound 1 | 60 | 0-27 | p.o. | 10 |

The anti-tumor effect of the drug was evaluated according to tumor growth inhibition (TGI), which was calculated by the following equation.

TGI=(100%×[1−(TV of treated group on Day 27−TV of treated group on Day 0)/(TV of control group on Day 27−TV of control group on Day 0)])

In addition, the presence of toxicity was judged as follows: a dose observed with a weight loss of 20% or more or a mortality rate of 10% or more was judged to have exceeded the MTD (maximum tolerated dose) and thus toxicity was present.

Figure 2:
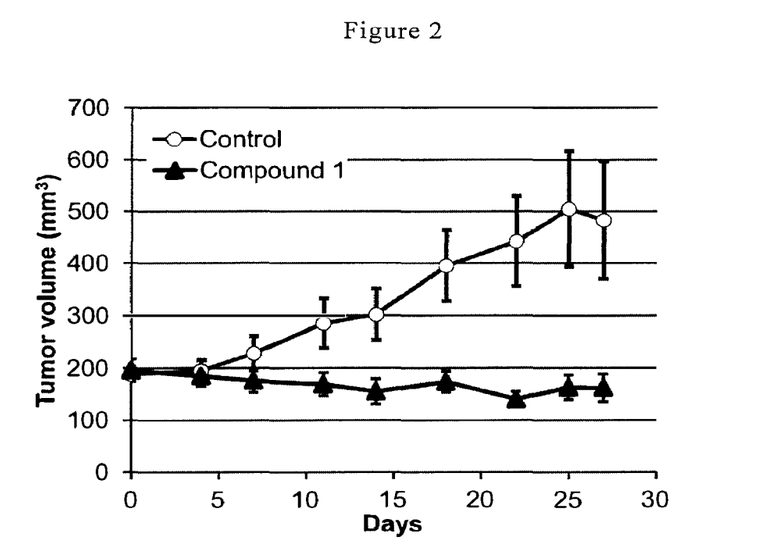
FIG. 2 shows an anti-tumor effect of Compound 1 on mouse models transplanted with a tissue derived from a breast cancer patient who is resistant to existing chemotherapies.

The results are shown in Table 10 below and in FIG. 2.

TABLE 10

| Group | TV (mm$^3$) on Day0 Mean ± SD | TV (mm$^3$) on Day27 Mean ± SD | p-value a) vs. Control | TGI(%) | BWG(%) on Day27 Mean |
|---|---|---|---|---|---|
| Control | 189 ± 14 | 483 ± 114 | — | — | 2.85 |
| Compound 1 | 196 ± 22 | 162 ± 27 | 0.0056 | 112 | −0.60 |

$^{a)}$: p-value was calculated by the One-way ANOVA followed by Dunnett's multiple comparisons test
SD: standard deviation On Day 27, TV of the Compound-1-administered group was shown to be significantly lower than that of the control-administered group.

Furthermore, since the average rate of change in the weight during the administration period did not decrease by 5% or more in the Compound-1-administered group, the dose was judged to be tolerable.

From the above-described results, the pyrazolo[3,4-d]pyrimidine compound represented by General formula (I) or a salt thereof that is used in the present invention was found to exert a superior anti-tumor effect to a IHER2-positive tumor which is resistant or intractable to other antitumor agents.

The invention claimed is:

1. A method of treating a subject with a HER2-positive tumor which is resistant or intractable to an anti-HER2 antibody, the method comprising a step of administering to said subject an effective amount of a pyrazolo[3,4-d]pyrimidine compound represented by formula 1 below or a salt thereof:

[formula 1]

(wherein, X represents a saturated, optionally substituted nitrogen-containing 4-10-membered heterocyclic group;

Y represents —C($R_4$)=C($R_5$)($R_6$);

$Z_1$, $Z_2$, $Z_3$ and $Z_4$ identically or differently represent a hydrogen atom, a halogen atom, a cyano group, a C2-C6 alkenyl group, an optionally substituted C1-C6 alkoxy group, an optionally substituted C1-C6 alkyl group, an optionally substituted amino group, an optionally substituted C3-C7 cycloalkyl group, a C6-C14 aromatic hydrocarbon group or an unsaturated 4-14-membered heterocyclic group, or $Z_1$ and $Z_2$ or $Z_3$ and $Z_4$ may form, together with carbon atoms that bind thereto, a benzene ring or a saturated or unsaturated 5-7-membered heterocycle;

W represents —$CH_2$—, an oxygen atom or —NH—;

n represents an integer of 0 to 2;

$R_1$ represents an optionally substituted amino group;

$R_2$ and $R_3$ identically or differently represent a hydrogen atom, an optionally substituted C1-C6 alkoxy group, an optionally substituted C1-C6 alkyl group or an optionally substituted C6-C14 aromatic hydrocarbon group, or $R_2$ and $R_3$ may form, together with a nitrogen atom that binds thereto, a saturated, optionally substituted nitrogen-containing 4-8-membered heterocyclic group; and $R_4$, $R_5$ and $R_6$ identically or differently represent a hydrogen atom or an optionally substituted C1-C6 alkyl group).

2. The method of claim 1 wherein the compound of formula 1 is (R)-1-(1-acryloylpiperidine-3-yl)-4-amino-N-(4-(2-(dimethylamino)-2-oxoethyl)-2,3-dimethylphenyl)-1H-pyrazolo [3,4-d]pyrimidine-3-carboxamide.

3. The method of claim 1, wherein the pyrazolo[3,4-d] pyrimidine compound is a compound selected from:
(1) (R)-1-(1-acryloylpiperidine-3-yl)-4-amino-N-(5-bromo-4-(2-(dimethylamino)-2-oxoethyl)-2-methylphenyl)-1H-pyrazolo[3,4-d]pyrimidine-3-carboxamide;
(2) (R)-1-(1-acryloylpiperidine-3-yl)-4-amino-N-(2-chloro-4-(2-(dimethylamino)-2-oxoethyl)-5-methylphenyl)-1H-pyrazolo[3,4-d]pyrimidine-3-carboxamide;
(3) (R)-1-(1-acryloylpiperidine-3-yl)-4-amino-N-(2-chloro-4-(2-(dimethylamino)-2-oxoethyl)-3-methylphenyl)-1H-pyrazolo[3,4-d]pyrimidine-3-carboxamide;
(4) (R)-1-(1-acryloylpiperidine-3-yl)-4-amino-N-(4-(2-(dimethylamino)-2-oxoethyl)-2-methylphenyl)-1H-pyrazolo[3,4-d]pyrimidine-3-carboxamide;
(5) (R)-1-(1-acryloylpiperidine-3-yl)-4-amino-N-(4-(2-(dimethylamino)-2-oxoethyl)naphthalene-1-yl)-1H-pyrazolo[3,4-d]pyrimidine-3-carboxamide;
(6) (R)-1-(1-acryloylpiperidine-3-yl)-4-amino-N-(2-chloro-4-(2-(dimethylamino)-2-oxoethyl)phenyl)-1H-pyrazolo[3,4-d]pyrimidine-3-carboxamide;
(7) (R)-1-(1-acryloylpiperidine-3-yl)-4-amino-N-(4-(2-(dimethylamino)-2-oxoethyl)-2-methoxyphenyl)-1H-pyrazolo[3,4-d]pyrimidine-3-carboxamide;
(8) (R)-1-(1-acryloylpiperidine-3-yl)-4-amino-N-(3-chloro-4-(2-(dimethylamino)-2-oxoethyl)phenyl)-1H-pyrazolo[3,4-d]pyrimidine-3-carboxamide;
(9) (R)-1-(1-acryloylpiperidine-3-yl)-4-amino-N-(5-chloro-4-(2-(dimethylamino)-2-oxoethyl)-2-methoxyphenyl)-1H-pyrazolo[3,4-d]pyrimidine-3-carboxamide;
(10) (R)-1-(1-acryloylpiperidine-3-yl)-4-amino-N-(4-(2-(dimethylamino)-2-oxoethyl)-5-fluoro-2-methylphenyl)-1H-pyrazolo[3,4-d]pyrimidine-3-carboxamide;
(11) (R)-1-(1-acryloylpiperidine-3-yl)-4-amino-N-(3-chloro-4-(2-(dimethylamino)-2-oxoethyl)-2-methoxyphenyl)-1H-pyrazolo[3,4-d]pyrimidine-3-carboxamide;
(12) (R)-1-(1-acryloylpiperidine-3-yl)-4-amino-N-(4-(2-(dimethylamino)-2-oxoethyl)-3-fluoro-2-methylphenyl)-11H-pyrazolo[3,4-d]pyrimidine-3-carboxamide;
(13) (R)-1-(1-acryloylpiperidine-3-yl)-4-amino-N-(4-(2-(dimethylamino)-2-oxoethyl)-2,3-dimethylphenyl)-1H-pyrazolo[3,4-d]pyrimidine-3-carboxamide;
(14) (R)-1-(1-acryloylpiperidine-3-yl)-4-amino-N-(4-(2-(dimethylamino)-2-oxoethyl)-3-fluoro-2-methoxyphenyl)-1H-pyrazolo[3,4-d]pyrimidine-3-carboxamide;
(15) (R)-1-(1-acryloylpiperidine-3-yl)-4-amino-N-(2-(difluoromethoxy)-4-(2-(dimethylamino)-2-oxoethyl)phenyl)-1H-pyrazolo[3,4-d]pyrimidine-3-carboxamide;
(16) (R)-1-(1-acryloylpiperidine-3-yl)-4-amino-N-(4-(2-(dimethylamino)-2-oxoethyl)-2-(fluoromethoxy)phenyl)-1H-pyrazolo[3,4-d]pyrimidine-3-carboxamide;
(17) (R)-1-(1-acryloylpiperidine-3-yl)-4-amino-N-(2-bromo-4-(2-(dimethylamino)-2-oxoethyl)phenyl)-1H-pyrazolo[3,4-d]pyrimidine-3-carboxamide;
(18) (R)-1-(1-acryloylpiperidine-3-yl)-4-amino-N-(2-chloro-4-(2-(dimethylamino)-2-oxoethyl)-5-fluorophenyl)-1H-pyrazolo[3,4-d]pyrimidine-3-carboxamide;
(19) (R)-1-(1-acryloylpiperidine-3-yl)-4-amino-N-(5-chloro-4-(2-(dimethylamino)-2-oxoethyl)-2-methylphenyl)-1H-pyrazolo[3,4-d]pyrimidine-3-carboxamide; and
(20) (R)-1-(1-acryloylpiperidine-3-yl)-4-amino-N-(2,5-dichloro-4-(2-(dimethylamino)-2-oxoethyl)phenyl)-1H-pyrazolo[3,4-d]pyrimidine-3-carboxamide.

4. The method of claim 1, wherein the resistance or intractability to other antitumor agents is resistance or intractability that is acquired via a treatment with a HER2 inhibitor.

5. The method of claim 1, wherein the resistance or intractability to other antitumor agents is intrinsic resistance or intractability irrelevant to a treatment with a HER2 inhibitor.

6. The method of claim 1, wherein the HER2 inhibitor is an anti-HER2 antibody.

7. The method of claim 1, wherein the anti-HER2 antibody is at least one selected from the group consisting of trastuzumab, trastuzumab emtansine and pertuzumab.

* * * * *